United States Patent
Tan et al.

(10) Patent No.: US 12,344,881 B2
(45) Date of Patent: Jul. 1, 2025

(54) GENETIC ENGINEERING BACTERIUM FOR DE NOVO SYNTHESIS OF CIS,CIS-MUCONIC ACID BY TAKING GLUCOSE AS SUBSTRATE AND APPLICATIONS THEREOF

(71) Applicant: Beijing University of Chemical Technology, Beijing (CN)

(72) Inventors: Tianwei Tan, Beijing (CN); Menglei Li, Beijing (CN)

(73) Assignee: Beijing University of Chemical Technology, Beijing (CN)

( * ) Notice: Subject to any disclaimer, the term of this patent is extended or adjusted under 35 U.S.C. 154(b) by 0 days.

(21) Appl. No.: 18/825,195

(22) Filed: Sep. 5, 2024

(65) Prior Publication Data
US 2024/0425889 A1    Dec. 26, 2024

Related U.S. Application Data

(63) Continuation of application No. PCT/CN2024/095637, filed on May 28, 2024.

(30) Foreign Application Priority Data

Sep. 27, 2023   (CN) .......................... 202311253745.4

(51) Int. Cl.
| | | |
|---|---|---|
| *C12P 7/44* | (2006.01) | |
| *C12N 9/02* | (2006.01) | |
| *C12N 9/10* | (2006.01) | |
| *C12N 9/88* | (2006.01) | |
| *C12N 9/90* | (2006.01) | |
| *C12N 15/52* | (2006.01) | |
| *C12N 15/77* | (2006.01) | |

(52) U.S. Cl.
CPC .............. *C12P 7/44* (2013.01); *C12N 9/0069* (2013.01); *C12N 9/1022* (2013.01); *C12N 9/1085* (2013.01); *C12N 9/88* (2013.01); *C12N 9/90* (2013.01); *C12N 15/52* (2013.01); *C12N 15/77* (2013.01); *C12Y 113/11001* (2013.01); *C12Y 202/01001* (2013.01); *C12Y 401/01061* (2013.01); *C12Y 401/01063* (2013.01); *C12Y 402/0101* (2013.01); *C12Y 402/03004* (2013.01)

(58) Field of Classification Search
None
See application file for complete search history.

(56) References Cited

U.S. PATENT DOCUMENTS

| | | | | |
|---|---|---|---|---|
| 6,210,937 | B1 * | 4/2001 | Ward .................... | C12N 15/52 |
| | | | | 435/232 |
| 2015/0005490 | A1 | 1/2015 | Harada et al. | |
| 2021/0079371 | A1 | 3/2021 | Zhang et al. | |
| 2022/0348939 | A1 | 11/2022 | Yang et al. | |

OTHER PUBLICATIONS

Li et al., Corynebacterium glutamicum cell factory design for the efficient production of cis, cis-muconic acid, Metabolic Eng. 82, Feb. 2024, 225-37. (Year: 2024).*
Genbank, Accession No. AB479384.2, 2014, www.ncbi.nlm.nih.gov. (Year: 2014).*
Genbank, Accession No. NC_011283.1, 2023, www.ncbi.nlm.nih.gov, part 1. (Year: 2023).*
Genbank, Accession No. NC_011283.1, 2023, www.ncbi.nlm.nih.gov, part 2. (Year: 2023).*
Genbank, Accession No. NC_006958.1, 2022, www.ncbi.nlm.nih.gov. (Year: 2022).*
Genbank, Accession No. NC_022040.1, 2023, www.ncbi.nlm.nih.gov, part 1. (Year: 2023).*
Genbank, Accession No. NC_022040.1, 2023, www.ncbi.nlm.nih.gov, part 2. (Year: 2023).*
Uniprot, Accession No. P35170, 2022, www.uniprot.org. (Year: 2022).*
Genbank, Accession No. MK238521.1, 2019, www.ncbi.nlm.nih.gov. (Year: 2019).*
Park et al., Shikimate metabolic pathway engineering in Corynebacterium, J. Microbiol. Biotechnol. 31, 2021, 1305-10. (Year: 2021).*
Lee et al., Corynebacterium Cell Factory Design and Culture Process Optimization for Muconic Acid Biosynthesis, Sci. Reports 8, 2018, 18041. (Year: 2018).*
Zhang et al., Application of CRISPRi in Corynebacterium glutamicum for shikimic acid production, Biotechnol. Lett. 38, 2016, 2153-61. (Year: 2016).*
CNIPA, Notification of First Office Action for Chinese application CN202311253745.4, Nov. 13, 2023.
CNIPA, Notification to grant patent right for Chinese application CN202311253745.4, Nov. 30, 2023.

* cited by examiner

*Primary Examiner* — Todd M Epstein

(74) *Attorney, Agent, or Firm* — Hemisphere Law, PLLC; Zhigang Ma

(57) ABSTRACT

The present invention discloses a genetic engineering bacterium for de novo synthesis of cis,cis-muconic acid by taking glucose as a substrate and applications thereof, and belongs to the technical field of genetic recombination and metabolic engineering. The genetic engineering bacterium for de novo synthesis of cis,cis-muconic acid (MA) by taking glucose as the substrate disclosed in the present invention is modified with chassis microbes, and includes recombinant *Corynebacterium glutamicum* for a cis,cis-muconic acid pathway construction module and an intermediate high-yield module. Production capacity of strains is greatly improved; MA of 90.2 g/L is finally obtained in fermentation liquor; and possibilities are provided for green and low-cost production of numerous chemicals such as adipic acid and nylon-66.

5 Claims, 5 Drawing Sheets

Specification includes a Sequence Listing.

```
                              SEQUENCE LISTING

Sequence total quantity: 85
SEQ ID NO: 1            moltype = DNA   length = 1032
FEATURE                 Location/Qualifiers
source                  1..1032
                        mol_type = genomic DNA
                        organism = Corynebacterium glutamicum
SEQUENCE: 1
cttttccag agcttttgg aacagcttgc cggtgacacc gtcaatattt ccactgatgt      60
acgtacgccc gtccacgtgg cggaaagtca aggtgccatc actcccctt ggcccacgct   120
tctttcctgt gaaggttgga tccagttcct tgatccagcg agtaatcagc cctgcaagtg   180
cggaggcttc catcagtgcc tggccagcaa tgcgcggtgt cagcttttcg gcaatgcgat   240
ggtccaactc atcccacaac tccggtttag cctgcttgac tgcctgcata atgcgggcca   300
ggtacggaat ccgaacgtgg aagtgagttt ctaccaccac tcttaaaatg ggcagcttca   360
ttaaagccca catggcgtta atagcctggt tgataaaatg cttggattcc cccgtgacgg   420
ttttcaactc catgacaaga gtgctagcgt ccgcctctgg gtttgagatc agcaaagtcc   480
agcgctggat ctccatttgc gccatgtgta agttgatgtg actctctgga ttatttgggt   540
cctgatggct gaagtatgac atttccatgc cccctaatgg tttaaatttc ccctttttaa   600
ctcattagca cccaccctaa ccacacaaat caaaacaaac aagtgttcta acgaatattt   660
gttctaattc ttgaaaataa agataccgct ctaccgaaac tgcaggtaga gcggttagaa   720
cctcaactat cccttgaggt aatactccag agcattgggg tgttttgcca gtggagtgat   780
cttgacattc atgtatttga acatcggaaa gccactaaga attgcatgca gctcgtcgtg   840
gtcatcgaca tcgaaaatgg agtagtttgc atactcgccg acgactcgcc agattgcttt   900
catgattcca cgggattgca ggtctccgga gtaggccttt tccttagcct ggaaatctgc   960
catcacatcg gcgtccatgg aatcagggaa gacgacgtcc atgcgtgcta gaaacagcat  1020
cgataattct cc                                                      1032

SEQ ID NO: 2            moltype = DNA   length = 1033
FEATURE                 Location/Qualifiers
source                  1..1033
                        mol_type = genomic DNA
                        organism = Corynebacterium glutamicum
SEQUENCE: 2
tttttctatg gctttctggt taagtgggaa aagtcccgcc acaagatgtg gtcgggactt    60
caatgctagc taggtagaaa aactagtctt ccttatccag gacgaatggg tagtgaacgt   120
ggttaccatc ctcgccagtc tcagggtgca ggaccagttc tggcttcaca gcggttgcaa   180
cgtcgttttc gacccactcg ccaccctcga gtaaagctg ggtggtgatg gtgcggtagc    240
ccgggtggga aacgcgaag tggaggtggg ctgggcgcca tgggtgccca ccgtaagact    300
caatgaacca accggttggg ccatcatgag ggatctggta aggcgcaggc tgcagggtct   360
tgatcttgta gcggccttcc tcatcggtaa cgatggtgcc acgcaggttc cactctggga   420
ttccaggcgc gaactgggag tagtatccgt cctcatctgc gtgccagagc tcaacttctg   480
ctccatcaag accgttgccg tcgaggtcag taacctgccc ctcgaagatc agtggggtgc   540
atgcgcggtc cttgtcacga attggcattt cagcatccca agggagcttc ggagagttct   600
ctacgtaata agggccttcg atggaaccct tggttccggt gtagtcgtgg cggttgtagt   660
tgatctcttc gatctcatgc tcaacgaaaa cgtccaacca cagtggccac tcgccgtatt   720
ctccaacgtc gatcatccac tgcttgagca ctgcgtactc ttcgtaggtg acttcgtgct   780
tgtgagcaac ctgggcgatc gccgcgagca gatctacgta gatcgcgttt gcgcgttcct   840
tggaggtatc ggaggaaacg cggtttgcct tgaacttgtc agttgccttg ttgcccgaat   900
cgtgggctgt tggatcaacg atctgttcag ctgaagtcat gtcatactcc tagagacttt   960
gggggtgaag taggggggtgc gagtcggatc actgcctagc ggaaaaatct ttgtgatcgg  1020
ctgaactcga taa                                                     1033

SEQ ID NO: 3            moltype = DNA   length = 34
FEATURE                 Location/Qualifiers
source                  1..34
                        mol_type = other DNA
                        organism = synthetic construct
SEQUENCE: 3
ctagactttt tccagagctt tttggaacag cttg                                34

SEQ ID NO: 4            moltype = DNA   length = 48
FEATURE                 Location/Qualifiers
source                  1..48
                        mol_type = other DNA
                        organism = synthetic construct
SEQUENCE: 4
ccagaaagcc atagaaaaag gagaattatc gatgctgttt ctagcacg                 48

SEQ ID NO: 5            moltype = DNA   length = 31
FEATURE                 Location/Qualifiers
source                  1..31
                        mol_type = other DNA
                        organism = synthetic construct
```

```
SEQUENCE: 5
tttttctatg gctttctggt taagtgggaa a                                          31

SEQ ID NO: 6            moltype = DNA   length = 32
FEATURE                 Location/Qualifiers
source                  1..32
                        mol_type = other DNA
                        organism = synthetic construct
SEQUENCE: 6
ttatcgagtt cagccgatca caaagatttt tc                                         32

SEQ ID NO: 7            moltype = DNA   length = 35
FEATURE                 Location/Qualifiers
source                  1..35
                        mol_type = other DNA
                        organism = synthetic construct
SEQUENCE: 7
atcggctgaa ctcgataaaa gcttggcact ggccg                                      35

SEQ ID NO: 8            moltype = DNA   length = 41
FEATURE                 Location/Qualifiers
source                  1..41
                        mol_type = other DNA
                        organism = synthetic construct
SEQUENCE: 8
caaaaagctc tggaaaaagt ctagaggatc cccgggtacc g                               41

SEQ ID NO: 9            moltype = DNA   length = 23
FEATURE                 Location/Qualifiers
source                  1..23
                        mol_type = other DNA
                        organism = synthetic construct
SEQUENCE: 9
ctcaagcgtt tgcgaaagaa acg                                                   23

SEQ ID NO: 10           moltype = DNA   length = 26
FEATURE                 Location/Qualifiers
source                  1..26
                        mol_type = other DNA
                        organism = synthetic construct
SEQUENCE: 10
gagtcagtga acaggtacca tttgcc                                                26

SEQ ID NO: 11           moltype = DNA   length = 1003
FEATURE                 Location/Qualifiers
source                  1..1003
                        mol_type = genomic DNA
                        organism = Corynebacterium glutamicum
SEQUENCE: 11
gctcaccgcg attttagagt ggcgaaactc tcattcttta ccgttagcaa ccctatgggg            60
tctcatcagc tgcgccttac cttttgcggg gccacttttc tggattgtta taagctactt           120
taagaataga aaaaaataaa agaatcaaag cgaagtgcta tttacttgat tcacccgttg           180
ataaatattt attcatatat tgaagttctc ggcatacatt cccataaaag ctcataaact           240
ctgtgtcgtg acctctcaga ttattatgat gagttttccc ttttcacgt aattgaatta            300
gcacgaaggg cgattcccaa atgaccaatg ggtcggatcg ccttttttgct catgctcagt          360
tcactggcgt acagcgcaca gttacatttc gaccagatag cgcactggat gcactgtcgt           420
gattacttac ttctcagcta tagacatact ttcgctactt attctcagcg tcattatgct           480
catctgcagt gcgccagtct tattagtcat ctttcgcagc aacagtcctg acgacctcat           540
cgcagcactc atcctgacag cgttgttggg ttttctcgct gtcaattttg tactccccac           600
actcgcagac atcggctgca cgctcgtcga gctttaaacc agtacccaa ccagaaagtg            660
actacgacat gagcgcaaaa tcccctaccc cacagcctcc gtacgaaata ccatcattcc           720
ggaaaagacg cctaatcact accgattat taacaatcac aacattgtgg ttcatctact            780
tttatgtgga tctagtaagc gccactacgc tacttacgct gccggtgatt atcgctgcac           840
cattgatcat ggtctacatc tggtaccacg aattcacata ctatctcgt gtccgaaaaa            900
acaataagct ttacaaggct ctctatgggc acctccaaaa ccatcaacat cctgaaaata           960
cggatactcc acccatgtaa aatagtcacta agatttagtc aca                          1003

SEQ ID NO: 12           moltype = DNA   length = 1024
FEATURE                 Location/Qualifiers
source                  1..1024
                        mol_type = genomic DNA
                        organism = Corynebacterium glutamicum
SEQUENCE: 12
tccgagagcc gagtaccgct taagtctcag gcataaatca agaactcaga gacgatccgg            60
caggacgaat gacatccaca ggttcaggct gatccgtcac ctcgatcaca tattgaacct           120
ctgagtccga accatccggg aaagtcactt ctgtacgaaa ccacagttga ccggttcgat           180
catcaggcgc cgtgaaggtg agatcgccag tcttctcatc tatgagaatg attgcaccca           240
tcaactccgc attctcaatt gagccgtaac gatctcggac caccttcgat ccctgtggga           300
ccccaccaac cgctcctgta ccaccatccg tcaccctcaa tgggatcttg acagtctgac           360
```

```
cattgcggac tttaggataa cccgtgcttt caatgccgta gtaaatactg tcagccacat    420
aaaccactga atggggtgtc actctatcaa atgaccatc  agggtagacc accttgacag    480
tcactcgatc tgtataagat cgtttcattt caccagggt  gtagctgatc cccgaagccc    540
caagagtatg tcgaatctcc cctgtatttg ggtccaatcg agaagcgagc agaccatcat    600
caataataat tgaaaacgaa tcaccctcaa gtaaaaatcg agtctcctct ggtaattcag    660
caaggttttc aacagactgt tcaaccgact tgggaaagac tccactagaa ccgagacgcg    720
tttctaagga ttcataccgt ggttcatact gagcagccat agacacattt tcatatgcaa    780
tcgcaacacc cgtgccattt accgttgctc cgaacaacag tgaacatgac agtgcagcgg    840
taaccaacgt gcgtgaacgt accaacatac ttctacacca cttttctaaat tagagatact    900
ctatgccacc tcacagtata ggtacaggat gtgtggcgtt ccctgccctc atggacgggg    960
ttgctgcgta ccaactgccc tacacattgc gagagccgga taacgcttaa gtctcaagca   1020
gaga                                                                1024

SEQ ID NO: 13           moltype = DNA  length = 26
FEATURE                 Location/Qualifiers
source                  1..26
                        mol_type = other DNA
                        organism = synthetic construct
SEQUENCE: 13
gtcgctcacc gcgattttag agtggc                                           26

SEQ ID NO: 14           moltype = DNA  length = 37
FEATURE                 Location/Qualifiers
source                  1..37
                        mol_type = other DNA
                        organism = synthetic construct
SEQUENCE: 14
gatgtgacta aatcttagtg actatttaca tgggtgg                               37

SEQ ID NO: 15           moltype = DNA  length = 38
FEATURE                 Location/Qualifiers
source                  1..38
                        mol_type = other DNA
                        organism = synthetic construct
SEQUENCE: 15
gtcactaaga tttagtcaca tccgagagcc gagtaccg                              38

SEQ ID NO: 16           moltype = DNA  length = 28
FEATURE                 Location/Qualifiers
source                  1..28
                        mol_type = other DNA
                        organism = synthetic construct
SEQUENCE: 16
tctctgcttg agacttaagc gttatccg                                         28

SEQ ID NO: 17           moltype = DNA  length = 38
FEATURE                 Location/Qualifiers
source                  1..38
                        mol_type = other DNA
                        organism = synthetic construct
SEQUENCE: 17
cttaagtctc aagcagagag acctgcaggc atgcaagc                              38

SEQ ID NO: 18           moltype = DNA  length = 39
FEATURE                 Location/Qualifiers
source                  1..39
                        mol_type = other DNA
                        organism = synthetic construct
SEQUENCE: 18
taaaatcgcg gtgagcgact ctagaggatc cccgggtac                             39

SEQ ID NO: 19           moltype = DNA  length = 1000
FEATURE                 Location/Qualifiers
source                  1..1000
                        mol_type = genomic DNA
                        organism = Corynebacterium glutamicum
SEQUENCE: 19
aacgttgacg gtgatgccat cgatgctggt tgcagccctg ctcactgctg agtgagtgac     60
agcagccaac tcgcgcagcg ttgcccactc cgcgtgccag ctgccggtgc cgcgctgcaa    120
acggcagtcg agggcgtcga aaagcgttgc aagaaggcca ggtgcccggc gcgcgtaacc    180
gtcgcacgca atcgcagcgg ccggattggc tttgtgggc  atcgcggagc tgccgccggg    240
ggatttctcc cgcaactcgc cgacctcggt tgtgagtaa  acaccacgt  caccagcaat    300
tttgcgtacc acaccagcgg ccgttgccag cgccgacgcg atcgcagtga tcggcgtgcg    360
atcggaaatgc cacacccact gcggatcaaa aaggcccaac tcctcggcca gcttcgcctg    420
aatctcgaag ccacgcgggt gcaccgccgt catatttccg ctggcaccgc catacgcacc    480
cggaaactcc agcgcctcca gggcgcgtgc gcattgtcc  accgcaacca gccagccgcc    540
ggtcagcgcg ccgaacgtcg tcggcgtcgc gatctgcccc aacgtgcgcc ccatgatcgg    600
ggttgcttta tgctccgcgg tgagctcggc caaatctcgc gcaagctttt taagcttgtc    660
gacgacctcc ccaccccttt ccttcatgca cagcattaac gcagaatcaa tgatgtcctg    720
```

```
gctcgttgcg ccaatgtgga tgcctgccgg attgatggcc ttgaggtcag tgaccagcgg   780
aatgagcgga ttaccgccct cggctgcgcg acgggaaagc tcctccacat ccaactgata   840
agaatcaatg gtggccttcg ccattgctgc gtgctcgggg gcagctgcaa ccgccaaagc   900
ggcctccacg acaagaagat tctttaggaa agtctcgtcg gaaaggctgc tgaggtgttc   960
tccactacca gcaaggtcgg agtataaaga tcgggtcaat                        1000

SEQ ID NO: 20           moltype = DNA   length = 1000
FEATURE                 Location/Qualifiers
source                  1..1000
                        mol_type = genomic DNA
                        organism = Corynebacterium glutamicum
SEQUENCE: 20
gcgagacctt tctgcgtcta gtgatataga tctcaaagta gggatgattg aggccgttga    60
caagtagttc gcggggcgaa catgtcagat cgcgcgcgaa cattcgccac cagcgcaaac   120
cccgaaggtc aggggttaac taggggtgtg cataagggtt tagtcatcca atacctcgag   180
tgaactgcgg agcttttcaa aagtcttctc catccgtgct tccagagtct gcccccactg   240
ccccgtgggc atctcttgcg ccaacggtcc gacaggttcg gttaccactg tgcgattgca   300
cggcccaatc caggcgaccc gacccatgga atcaatcgcc gcctggatgc gcccatcagt   360
cttcatattg tgatgatgcg cgcagaggca ctgcaagttc caggccacag tcaacccacc   420
ctcaccgaac gggatcacgt gatcgatctg cagttgtcg gcagacaccg tgcagcccgg    480
atgcctacag gtgccgtccc gccccatcac ataaaggcgt agctcgggac ttgggggtgta  540
gccatttttcc acacgagtgg cgatcgtatc caggtcaatg accttcgagg cagtcttacc  600
cagcttccgg gactcctctt gactcaggaa tccacccccc ggaatccagg acacgccacc   660
caccaggggc gtgtataccg cgctgacgat tttcactttg gtccgccccg ccaggaaggt   720
gaccagggcc cgcgcgaggt cctcgccctt ctgtttcact ttttccagag cttttttgaa   780
cagcttgccg gtgacaccgt caatatttcc actgatgtac gtagcccgt ccacgtggcg    840
gaaagtcaag gtgccatcac tcccctttgg cccacgcttc tttcctgtga aggttggatc   900
cagttccttg atccagcgag taatcagccc tgcaagtgcg gaggcttcca tcagtgcctg   960
gccagcaatg cgcggtgtca gctttttcggc aatgcgatgg                       1000

SEQ ID NO: 21           moltype = DNA   length = 21
FEATURE                 Location/Qualifiers
source                  1..21
                        mol_type = other DNA
                        organism = synthetic construct
SEQUENCE: 21
aacgttgacg gtgatgccat c                                              21

SEQ ID NO: 22           moltype = DNA   length = 29
FEATURE                 Location/Qualifiers
source                  1..29
                        mol_type = other DNA
                        organism = synthetic construct
SEQUENCE: 22
attgacccga tctttatact ccgaccttg                                      29

SEQ ID NO: 23           moltype = DNA   length = 44
FEATURE                 Location/Qualifiers
source                  1..44
                        mol_type = other DNA
                        organism = synthetic construct
SEQUENCE: 23
gagtataaag atcgggtcaa tgcgagacct tctgcgtct agtg                      44

SEQ ID NO: 24           moltype = DNA   length = 22
FEATURE                 Location/Qualifiers
source                  1..22
                        mol_type = other DNA
                        organism = synthetic construct
SEQUENCE: 24
ccatcgcatt gccgaaaagc tg                                             22

SEQ ID NO: 25           moltype = DNA   length = 35
FEATURE                 Location/Qualifiers
source                  1..35
                        mol_type = other DNA
                        organism = synthetic construct
SEQUENCE: 25
ttcggcaatg cgatgggacc tgcaggcatg caagc                               35

SEQ ID NO: 26           moltype = DNA   length = 29
FEATURE                 Location/Qualifiers
source                  1..29
                        mol_type = other DNA
                        organism = synthetic construct
SEQUENCE: 26
atcaccgtca acgttgactc tagaggatc                                      29

SEQ ID NO: 27           moltype = DNA   length = 1000
```

| FEATURE | Location/Qualifiers |
| --- | --- |
| source | 1..1000<br>mol_type = genomic DNA<br>organism = Corynebacterium glutamicum |

SEQUENCE: 27

```
caacagaggt gccgttgtca aagaattcct cccccttag gcgtgagacc agcatgtcca   60
gatcctcacg gactggaacg atcactgcta catcagcaag acccaaggtt gctgcgcgtg  120
gacctgcacc tgctgagttc caggtgttca tggccacatg gtggtgatat ccacctgcgg  180
aggcaaacag tgcattgggg attgatgtgg tggcatcaaa accaatcttg tccacataga  240
attgacgggc tcgctcgacg ttgcctacct gaaggtgaac gtgtccgatg ctcgcaggga  300
gaatagcggt gttgttcaaa acggtttcgc tgagatgact ctgaaggtac tggtttggat  360
ccaagtagat ggtgtccatg cggacatcgc cgttgtctgc atacttccat gcacttgcag  420
ggcggtcaac atagagctca atgccgtttc cctcaggatc ggtgaagtaa aaagcttcag  480
agactaggtg atctgaagaa cccacaaaac gtgagcgtga ttcttgcgct gcgcggtaaa  540
cggtggcagc caagctctct tgggtatcga agaggaaagc ggtgtgataa aggccagctt  600
gacgaggatc taccgcagga agacctgggg tagaaatcag gcgaagcagt ggggtgccat  660
tgcgaccgag tacacggtga acttctttc cgtgaacttt ttcttccatt ggttcaacgc  720
taaggattga agagtagtaa ctagtcatac cctctaggtc gccgacgcga aggctaactg  780
catccatgaa ggtgtcgcta ttgatgctct gctcaagaag tgccatggtg tttcatcctt  840
taagtgttgg tggctgtttt gctgttgaac accattgttc accaatttac tttccgtgtc  900
aagtaaaattc ttaaatgagg cggatttccc ctgccctagc cacgaaaaat gcgctgacac  960
cacgtacagt gtcaacgcat tttttgaaag atttaagcga                         1000
```

| SEQ ID NO: 28 | moltype = DNA length = 1001 |
| --- | --- |
| FEATURE | Location/Qualifiers |
| source | 1..1001<br>mol_type = genomic DNA<br>organism = Corynebacterium glutamicum |

SEQUENCE: 28

```
gcccataagc ctagtacgtc attccccctc aagccacagg tactaccatt aattctcgat   60
gaatcttgcg acccagagtg tgaacagaca atgttctacg cctctgacgt gcttaaatca  120
gaaaaaaccg ggcacccaca aaacaattcg ggcactcggt ttttctacca aaaacatctc  180
agccaggtca ggcctatggt tgaaacctat cgcgttgagg gcgtttctcc atcaatgccc  240
tcccctgctt tcggcaaggg ttttccatcc ggcgaagcta cagcatctgc tgcaacagac  300
gctgcgaaag tcggatctac ctcttcggga gtttccctac ccttcttcaa caggaagaac  360
acgatgatcg cgccggcaaa cactactgcg gagacgatgg tgttgattcg gatgccgcca  420
ataagcgtgc cttcatcaac gcgcatttgt tcaatccaga aacggcccaa ggtataacca  480
gctacgtaga gtgcaaatac tcggccatgt cccagcttga atcgcttgtc agcccacatc  540
aacaaagcga agatcagtag gttccacaac agttcataga ggaatgttgg atgaacagta  600
gccattactt caccggtgga tgttcctgtc accggtgcga attttccatt ttcatctacc  660
cgatagtaga ttttccaaagc ccatggaacg gtagtttctg caccgtagag ctcctggtta  720
aaccagttgc ccagacgacc aattccctgc gccaggataa ctgcaggtgc cacggcatct  780
gcgaaaggtg caagaggaag cttttgtac cggaagaata cggccactgc caggccaccg  840
aggatcactg caccccagat gcccagacca ccgttggtga ttttgaaggc gtcgacgggg  900
ttacaggtat cgcagaagta ctttttggttg tcggtaatga cgtgataaat gcgtccaccg  960
atgattccgg caggaactgc cacgatcgct gcatcaagga c                        1001
```

| SEQ ID NO: 29 | moltype = DNA length = 33 |
| --- | --- |
| FEATURE | Location/Qualifiers |
| source | 1..33<br>mol_type = other DNA<br>organism = synthetic construct |

SEQUENCE: 29

```
ctctagagtc caacagaggt gccgttgtca aag                                  33
```

| SEQ ID NO: 30 | moltype = DNA length = 35 |
| --- | --- |
| FEATURE | Location/Qualifiers |
| source | 1..35<br>mol_type = other DNA<br>organism = synthetic construct |

SEQUENCE: 30

```
ggctcgctta atctttcaa aaaatgcgtt gacac                                 35
```

| SEQ ID NO: 31 | moltype = DNA length = 40 |
| --- | --- |
| FEATURE | Location/Qualifiers |
| source | 1..40<br>mol_type = other DNA<br>organism = synthetic construct |

SEQUENCE: 31

```
gaaagattta agcgagccca taagcctagt acgtcattcc                           40
```

| SEQ ID NO: 32 | moltype = DNA length = 27 |
| --- | --- |
| FEATURE | Location/Qualifiers |
| source | 1..27<br>mol_type = other DNA<br>organism = synthetic construct |

SEQUENCE: 32

```
caggtcgtcc ttgatgcagc gatcgtg                                         27
```

```
SEQ ID NO: 33            moltype = DNA    length = 29
FEATURE                  Location/Qualifiers
source                   1..29
                         mol_type = other DNA
                         organism = synthetic construct
SEQUENCE: 33
catcaaggac gacctgcagg catgcaagc                                          29

SEQ ID NO: 34            moltype = DNA    length = 31
FEATURE                  Location/Qualifiers
source                   1..31
                         mol_type = other DNA
                         organism = synthetic construct
SEQUENCE: 34
ctctgttgga ctctagagga tccccgggta c                                       31

SEQ ID NO: 35            moltype = DNA    length = 858
FEATURE                  Location/Qualifiers
source                   1..858
                         mol_type = genomic DNA
                         organism = Corynebacterium glutamicum
SEQUENCE: 35
atgacttcag ctgaacagat cgttgatcca acagcccacg attcgggcaa caaggcaact         60
gacaagttca aggcaaaccg cgtttcctcc gatacctcca aggaacgcgc aaacgcgatc        120
tacgtagatc tgctcgcggc gatcgcccag gttgctcaca agcacgaagt cacctacgaa        180
gagtcgcag tgctcaagca gtggatgatc gacgttggaa atacggcgta tggccactg         240
tggttggacg ttttcgttga gcatgagatc gaagagatca actacaaccg ccacgactac        300
accggaacca agggttccat cgaaggccct tattacgtag agaactctcc gaagctccct        360
tgggatgctg aaatgccaat gcgtgacaag gaccgcgcat gcaccccact gatcttcgag        420
gggcaggtta ctgacctcga cggcaacggt cttgatggag cagaagttga gctctggcac        480
gcagatgagg acggatacta ctcccagttc gcgcctggaa tcccagagtg gaacctgcgt        540
ggcaccatcg ttaccgatga ggaaggccgc tacaagatca agaccctgca gcctgcgcct        600
taccagatcc ctcatgatgg cccaaccggt tggttcattg agtcttacgg tgggcaccca        660
tggcgcccag cccaccctcc acttgcgcgtt tcccaccccgg gctaccgcac catcaccacc        720
cagctttact tcgagggtgg cgagtgggtc gaaaacgacg ttgcaaccgc tgtgaagcca        780
gaactggtcc tgcaccctga gactggcgag gatggtaacc acgttcacta cccattcgtc        840
ctggataagg aagactag                                                     858

SEQ ID NO: 36            moltype = DNA    length = 15
FEATURE                  Location/Qualifiers
source                   1..15
                         mol_type = other DNA
                         organism = synthetic construct
SEQUENCE: 36
aaggaggata tacat                                                         15

SEQ ID NO: 37            moltype = DNA    length = 1509
FEATURE                  Location/Qualifiers
source                   1..1509
                         mol_type = genomic DNA
                         organism = Klebsiella pneumoniae
SEQUENCE: 37
atgaccgcac cgattcagga tctgcgcgac gccatcgcgc tgctgcaaca gcatgacaat         60
cagtatctcg aaaccgatca tccggttgac cctaacgccg agctggccgg tgtttatcgc        120
catatcggcg cgggcggcac cgtgaagcgc cccaccccgc tcgggccggc gatgatgttt        180
aacaatatta agggttatcc acactcgcgc attctggtgg gtatgcacgc cagccgccaa        240
cgggccgcgc tgctgctggg ctgcgaagcc tcgcagctgg cccttgaagt gggtaaggcg        300
gtgaaaaaac cggtcgcgcc ggtggtcgtc ccggccagca gcgcccccctg ccaggaacag        360
atctttctgg ccgacgatcc ggattttgat ttgcgcaatc tgcttccggc gcccaccaac        420
acccctatcg acgcggcccc cttcttctgt ctgggcctgg cgctggccag cgatcccgtc        480
gacgcctcgc tgaccgacgt caccatccac cgcttgtgcg tccagggccg ggatgagctg        540
tcgatgtttc ttgccgccgg ccgccatatc gaagtgtttc gccaaaaggc cgaggccgcc        600
ggcaaaccgc tgccgataac catcaatatg ggtctcgatc cggccatcta tattggcgcc        660
tgcttcgaag ccctaccac gccgttcggc tataatgaac tgggcgtcgc cggcgcgctg        720
cgtcaacgtc cggtggagct ggttcagggc gtcagcgtcc cggagaaagc catcgcccgc        780
gccgagatcg ttatcgaagg tgagctgttg cctggcgtgc gcgtcagaga ggatcagcac        840
accaatagcg gccacgcgat gccggaattt cctggctact cggcggcgc taatccgtcg         900
ctgccggtaa tcaaagtcaa agcagtgacc atgcgaaaca atgcgattct gcagaccctg        960
gtgggaccgg gggaagagca taccaccctc gccggcctgc caacggaagc cggcgcgctg       1020
aatgccgtcg aggccgccat tccgggcttt ttacaaaatg tctacgccca caccgcgggt       1080
ggcgtaagt tcctcgggat cctgcaggtg aaaaaacgtc aacccgccga tgaaggccgg       1140
caggggcagg ccgcgctgct ggcgctggcg acctattccg agctaaaaaa tattattctg       1200
gttgatgaag atgtcgacat cttttgacagc gacgatatcc tgtgggcgat gaccaccgc        1260
atgcagggggg atgctcagcat tacgacaatc cccggcattc gcggtcacca gctgatccg       1320
tcccagacgc cggaatacag cccgtcgatc cgtggaaatg gcatcagctg caagaccatt       1380
tttgactgca cggtccctg ggcgctgaaa tcgcactttg agcgcgcgcc gtttgccgac         1440
gtcgatccgc gtccgtttgc accgagtat ttcgcccggc tggaaaaaaa ccagggtagc         1500
gcaaaataa                                                               1509
```

| | | |
|---|---|---|
| SEQ ID NO: 38 | moltype = DNA length = 594 | |
| FEATURE | Location/Qualifiers | |
| source | 1..594<br>mol_type = genomic DNA<br>organism = Klebsiella pneumoniae | |

SEQUENCE: 38
```
atgaaactga ttattgggat gacggggcc accggggcac cgcttggggt ggcattgctg   60
caggcgctgc gcgatatgcc ggaggtggaa acccatctgg tgatgtcgaa atgggccaaa  120
accaccatcg agctggaaac gccctggacg cgcgcgaag tggccgcgct ggcggacttt  180
tcccacagcc cggcagacca ggccgccacc atctcatccg gttcatttcg taccgacggc  240
atgatcgtta ttccctgcag tatgaaaacg cttgcaggca ttcgcgcggg ttatgccgaa  300
gggctggtgg gccgcgcggc ggacgtggtg ctcaaagagg ggcgcaagct ggtgttggtc  360
ccgcgggaaa tgccgctcag cacgatccat ctggagaaca tgctggcgct gtcccgcatg  420
ggcgtggcga tggtcccgcc gatgccagct tactacaacc acccggagac ggttgacgat  480
atcaccaatc atatcgtcac ccgggtgctg gatcagtttg gcctcgacta tcacaaagcg  540
cgccgctgga acggcttgcg cacggcagaa caatttgcac aggagatcga ataa         594
```

| | | |
|---|---|---|
| SEQ ID NO: 39 | moltype = DNA length = 237 | |
| FEATURE | Location/Qualifiers | |
| source | 1..237<br>mol_type = genomic DNA<br>organism = Klebsiella pneumoniae | |

SEQUENCE: 39
```
atgatttgtc cacgttgcgc cgatgaaaag attgaagtca tggcgacctc gccggtgaaa   60
ggggtctgga ccgtgtatca gtgccagcac tgtctttaca cctggcgaga taccgagccg  120
ctgcgccgca ccagccgcga acactatccg gaagcgttcc gcatgacgca gaaagatatc  180
gatgaggcgc gcaggtgcc gcacgtaccg ccgctattgc cggaagataa gcgttaa      237
```

| | | |
|---|---|---|
| SEQ ID NO: 40 | moltype = DNA length = 31 | |
| FEATURE | Location/Qualifiers | |
| source | 1..31<br>mol_type = other DNA<br>organism = synthetic construct | |

SEQUENCE: 40
```
catatgactt cagctgaaca gatcgttgat c                                   31
```

| | | |
|---|---|---|
| SEQ ID NO: 41 | moltype = DNA length = 28 | |
| FEATURE | Location/Qualifiers | |
| source | 1..28<br>mol_type = other DNA<br>organism = synthetic construct | |

SEQUENCE: 41
```
ctagtcttcc ttatccagga cgaatggg                                       28
```

| | | |
|---|---|---|
| SEQ ID NO: 42 | moltype = DNA length = 56 | |
| FEATURE | Location/Qualifiers | |
| source | 1..56<br>mol_type = other DNA<br>organism = synthetic construct | |

SEQUENCE: 42
```
cctggataag gaagactaga aggaggatat acatatgacc gcaccgattc aggatc        56
```

| | | |
|---|---|---|
| SEQ ID NO: 43 | moltype = DNA length = 63 | |
| FEATURE | Location/Qualifiers | |
| source | 1..63<br>mol_type = other DNA<br>organism = synthetic construct | |

SEQUENCE: 43
```
atcccaataa tcagtttcat atgtatatcc tcctttatt ttgcgctacc ctggttttt      60
tcc                                                                  63
```

| | | |
|---|---|---|
| SEQ ID NO: 44 | moltype = DNA length = 30 | |
| FEATURE | Location/Qualifiers | |
| source | 1..30<br>mol_type = other DNA<br>organism = synthetic construct | |

SEQUENCE: 44
```
catatgaaac tgattattgg gatgacgggg                                     30
```

| | | |
|---|---|---|
| SEQ ID NO: 45 | moltype = DNA length = 28 | |
| FEATURE | Location/Qualifiers | |
| source | 1..28<br>mol_type = other DNA<br>organism = synthetic construct | |

SEQUENCE: 45
```
ttattcgatc tcctgtgcaa attgttct                                       28
```

| | | |
|---|---|---|
| SEQ ID NO: 46 | moltype = DNA length = 53 | |
| FEATURE | Location/Qualifiers | |

```
source                     1..53
                           mol_type = other DNA
                           organism = synthetic construct
SEQUENCE: 46
gcacaggaga tcgaataaaa ggaggatata catatgattt gtccacgttg cgc              53

SEQ ID NO: 47              moltype = DNA   length = 28
FEATURE                    Location/Qualifiers
source                     1..28
                           mol_type = other DNA
                           organism = synthetic construct
SEQUENCE: 47
gattaacgct tatcttccgg caatagcg                                          28

SEQ ID NO: 48              moltype = DNA   length = 40
FEATURE                    Location/Qualifiers
source                     1..40
                           mol_type = other DNA
                           organism = synthetic construct
SEQUENCE: 48
cggaagataa gcgttaatct agagtcgacc tgcaggcatg                             40

SEQ ID NO: 49              moltype = DNA   length = 57
FEATURE                    Location/Qualifiers
source                     1..57
                           mol_type = other DNA
                           organism = synthetic construct
SEQUENCE: 49
gttcagctga agtcatatgt atatcctcct tgagctcgaa ttcttctgtt tcctgtg          57

SEQ ID NO: 50              moltype = DNA   length = 1857
FEATURE                    Location/Qualifiers
source                     1..1857
                           mol_type = genomic DNA
                           organism = Corynebacterium glutamicum
SEQUENCE: 50
atgcgtacat ccattgccac tgtttgtttg tccggaactc ttgctgaaaa gctgcgcgca       60
gctgcagatg ctggatttga tggtgtgaa atcttcgagc aggacttggt ggtttccccg        120
cattcggcag agcagattcg tcagcgggct caggatttgg gattaaccct ggatctgttc       180
cagccgtttc gagatttcga aggtgtgaa gaagagcagt ttctgaagaa tctgcaccgc        240
ttggaagaga agttcaagct gatgaacagg cttggcattg agatgatctt gttgtgttcc      300
aatgtgggca ccgcgaccat caatgatgat gacctttcg tggagcagtt gcatcgtgca       360
gcagatttgg ctgagaagta caactgcaag attgcttatg aagcgttggc tgtggggcag      420
tttgtcaatg attttgagca tgcgcatgca cttgtggaga aggtgaatca caaggcgctg      480
ggaacctgct tggatacgtt ccatattctt tcccgtggtt gggaaaccga cgaggtggag      540
aacatccctc ggagaagat cttctttgtt cagttagcgg atgcgccgaa gctgagcatg       600
gacatttgt cctggtcgcg tcaccaccgt gttttccctg gtgaaggcga tttcgatctg       660
gtgaaattca tggttcatct ggccaagacg ggttatgatg gcccgatttc tttgagatc       720
ttcaacgatt ccttccgcaa ggccgaggtt ggtcgcaccg cgattgatgg gttgcgttct      780
ttgcgttggt tggaagatca gacctggcat gcgctaaatg ctgaggatcg tccaagcgct      840
cttgaactgc gtgcacttcc tgaggtcgcg gaacctgagg gtgttgattt cattgagatc      900
gccactggac gtttgggtga gaccattcgg gttcttcatc aattgggttt ccgcttgggt      960
ggtcatcact gcagtaagca ggattaccag gtatggaccc agggcgatgt gcgcattgtg      1020
gtgtgtgatc gtgggggtcac cggggctcca accacgatct ctgcgatggg ctttgacacc    1080
cccgatccag aagctgctca tgcccgtgcg gaattgctgc gggctcagac aattgatcgt      1140
ccccacatcg agggcgaagt tgacctaaaa ggtgtgtacg caccggatgg ggtggagctg      1200
ttttcgcgg ggccgagccc cgatggaatg cccgagtggc tgccggaatt cggcgtcgaa      1260
aagcaagaag ctggtctcat tgaagccatc gaccacgtca atttcgccca gccgtggcaa     1320
cattttgatg aggcagtgct gttttacacc gcgctgatgg cgttggagac tgtgcgtgag    1380
gatgagttcc cgagcccaat tggtttggtg cgcaatcagg tgatgcgttc gccgaatgat    1440
gcggtgcggt tgctgctcag cgtggcgccg gaggacggtg agcagggaga tttcctcaac    1500
gcggcctacc cggagcacat tgcgttggcc acggcggaca tcgtggcggt ggctgaacgt    1560
gcgcgcaaac gaggcctgga tttcttgccc gtcccagaga attactacga cgatgtgcag   1620
gcgcgttttg atttgccgca ggaattcttg gacacactca aggaaaacca cctgctttac    1680
gaccgcgacg agaacggcga attcctccac ttttacaccc gcacgttggg cacgctgttc   1740
ttcgaagtgg tggaacgccg cggcggtttt gcaggttggg gcgaaacaaa cgctccggtg    1800
cggttggcgc gcagtatcg tgaggtgcgg gacctcgagc ggggaatccc aaactag       1857

SEQ ID NO: 51              moltype = DNA   length = 1098
FEATURE                    Location/Qualifiers
source                     1..1098
                           mol_type = genomic DNA
                           organism = Corynebacterium glutamicum
SEQUENCE: 51
atgagcgcag tgcagatttt caacaccgtc acgtcaatg gatcttcccc ctatgatgtc        60
cacattggtt ccggcctcaa cgagctcatt gttcagcgcg cagcggaatc aggcgcggag       120
caggtagcga ttttgcacca gcccagcatg gatgacattg catccgagtt ggatgcagca      180
ctagtcgctg ctggtttgaa ggtcctgcac cttaatgttc ccgatgcgga aaacggcaag      240
tccttggaag tagcggggca gtgctgggat gaattgggtg gcgcagcatt cggccgccgc      300
```

```
gatatcgtca tcggacttgg tggcggtgct gccacagatc tcgcgggatt cgtcgctgct  360
gcatggatgc gtggcgtgcg cgtcattcag gttccaacca ccttgttggc catggtggac  420
gctgcggtgg gcggcaagac tggcatcaat accgccgcag gcaagaacct tgtgggcgcg  480
ttccacgagc ctgacgcagt attcattgac accgatcgcc tagccaccct gcctgacgcg  540
gaaatcatcg cgggatccgc cgaaatcatc aaaactggtt tcatcgccga cccagaaatc  600
ctgcgccttt acgaaactga tcccgcagcc tgcctgaaga agaagtcga aggctcccac   660
ctacctgaac tgatttggcg ctccgtcacc gtcaagggct ccgtggtcgg ccaagacctc  720
aaagaatcta gcctgcgcga atcctcaac tacggacaca cctttgccca cgccgtcgaa   780
ctccgcgaaa acttccgctg cgccacggc aatgccgttg cagtgggcat gatgttcatc   840
gccaacctct cccacaagct cgggcttatc gacgcgcccc tcctcgagcg ccaccgctca  900
atcctggcgg ccatcggtct gcccacttcc tacgaaggcg gagccttcga cgagctttac  960
gacggtatga cccgcgacaa gaaaaaccgc gacggcaaca tccgcttcgt cgcactgacc 1020
gccgtgggcg aggttacccg cattgagggg ccctcaaaac aagatttaca gagtgcttat 1080
gaggcaatca gccactaa                                               1098

SEQ ID NO: 52          moltype = DNA   length = 438
FEATURE                Location/Qualifiers
source                 1..438
                       mol_type = genomic DNA
                       organism = Corynebacterium glutamicum
SEQUENCE: 52
atgcctggaa aaattctcct cctcaacggc ccaaacctga acatgctggg caaacgcgag   60
cctgacattt acggacacga caccttggaa gacgtcgtcg cgctggcaac cgctgaggct  120
gcgaagcacg gccttgaggt tgaggcgctg cagagcaatc acgaaggtga gctaatcgat  180
gcgctgcaca acgctcgcgg cacccacatc ggttgcgtga ttaaccccgg cggcctgact  240
cacacttcgg tggcgctttt ggatgctgtg aaggcgtctg agcttcctac cgttgaggtg  300
cacatttcca atccgcatgc ccgtgaagag ttccgccacc attcttacat ttccctcgcg  360
gcggtctccg ttatcgctgg cgctggcatc cagggttacc gtttcgcggt cgatatcctg  420
gcaaatctca aaaagtag                                                438

SEQ ID NO: 53          moltype = DNA   length = 1995
FEATURE                Location/Qualifiers
source                 1..1995
                       mol_type = genomic DNA
                       organism = Escherichia coli
SEQUENCE: 53
atgtcctcac gtaaagagct tgccaatgct attcgtgcgc tgagcatgga cgcagtacag   60
aaagccaaat ccggtcaccc gggggcccct atgggtatgg ctgacattgc cgaagtcctg  120
tggcgtgatt tcctgaaaca caacccgcag aatccgtcct gggcgtaccg tgaccgcttc  180
gtgctgtcca acggccacgg ctccatgctg atctacagcc tgctgcacct caccggttac  240
gatctgccga tggaagaact gaaaaacttc cgtcagctgc actctaaaac tccgggtcac  300
ccggaaagtg gggttacacc gctgggtgtg gaaaccacca ccggtccgct gggtcagggt  360
attgccaacg cagtcggtat ggcgattgca gaaaaaacgc tggccgcgca gtttaaccgt  420
ccgggccacg acattgtcga ccactacacc tacgccttca tgggcgacgg ctgcatgatg  480
gaaggcatct cccacgaagt tgctctctgc gcgggtacgc tgaagctggg taaactgatt  540
gcattctacg atgacaacgg tatttctatc gatggtcacg ttgaaggctg gttcaccgac  600
gacaccgcaa tgcgtttcga agcttacggc tggcacgtta ttcgcgacat cgacggtcat  660
gacgcggcat ctatcaaacg cgcagtagaa gaagcgcgcg cagtgactga caaaccttcc  720
ctgctgatgt gcaaaaccat catcggtttc ggttccccga acaaagcgg tacccacgac  780
tcccacggtg cgccgctggg cgacgctgaa attgccctga cccgcgaaca actgggctgg  840
aaatatgcgc cgttcgaaat cccgtctgaa atctatgctc agtgggatgc gaaagaagca  900
ggccaggcga aagaatccgc atggaacgag aaattcgctg cttacgcgaa agcttatccg  960
caggaagccg ctgaatttac ccgccgtatg aaaggcgaaa tgccgtctga cttcgacgct 1020
aaagcgaaag agttcatcgc taaactgcag gctaatccgg cgaaaatcgc cagccgtaaa 1080
gcgtctcaga atgctatcga agcgttcggt cgcgtctgc cggaattcct cggcggttct 1140
gctgacctgg cgccgtctaa cctgaccctg tggtctggtt ctaaagcaat caacgaagat 1200
gctgcgggta actacatcca ctacggtgtt cgcgagttcg gtatgaccgc gattgctaac 1260
ggtatctccc tgcacggtgg cttcctgccg tacacctcca ccttcctgat gttcgtggaa 1320
tacgcacgta acgccgtacg tatggctgcg ctgatgaaac agcgtcaggt gatggtttac 1380
acccacgact ccatcggtct gggcgaagac gggccgactc accagccggt tgagcaggtc 1440
gcttctctgc gcgtaacccc gaacatgtct acatggcgtc cgtgtgacca ggttgaatcc 1500
gcggtcgcgt ggaaatacgg tgttgagcgt caggacggcc cgaccgcact gatcctctcc 1560
cgtcagaacc tggcgcagca ggaacgaact gaagagcaac tggcaaacat cgcgcgcggt 1620
ggttatgtgc tgaaagactg cgccggtcag ccggaactga ttttcatcgc taccggttct 1680
gaagttgaac tggctgttgc tgcctacgaa aaactgactg ccgaaggcgt gaaagcgcgc 1740
gtggtgtcca tgtcgtctac cgacgcattt gacaagcagg atgctgctta ccgtgaatcc 1800
gtactgccga agcggttac tgcacgcgtt gctgtagaag cgggtattgc tgactactgg 1860
tacaagtatg ttggcctgaa cggtgctatc gtcggtatga ccaccttcgg tgaatctgct 1920
ccggcagagc tgctgtttga agagttcggc ttcactgttg ataacgttgt tgcgaaagca 1980
aaagaactgc tgtaa                                                  1995

SEQ ID NO: 54          moltype = DNA   length = 25
FEATURE                Location/Qualifiers
source                 1..25
                       mol_type = other DNA
                       organism = synthetic construct
SEQUENCE: 54
catatgcgta catccattgc cactg                                        25
```

```
SEQ ID NO: 55              moltype = DNA   length = 22
FEATURE                    Location/Qualifiers
source                     1..22
                           mol_type = other DNA
                           organism = synthetic construct
SEQUENCE: 55
ctagtttggg attccccgct cg                                           22

SEQ ID NO: 56              moltype = DNA   length = 56
FEATURE                    Location/Qualifiers
source                     1..56
                           mol_type = other DNA
                           organism = synthetic construct
SEQUENCE: 56
ggggaatccc aaactagaag gaggatatac atatgagcgc agtgcagatt ttcaac      56

SEQ ID NO: 57              moltype = DNA   length = 27
FEATURE                    Location/Qualifiers
source                     1..27
                           mol_type = other DNA
                           organism = synthetic construct
SEQUENCE: 57
cttttagtgg ctgattgcct cataagc                                      27

SEQ ID NO: 58              moltype = DNA   length = 48
FEATURE                    Location/Qualifiers
source                     1..48
                           mol_type = other DNA
                           organism = synthetic construct
SEQUENCE: 58
gcaatcagcc actaaaagga ggatatacat atgcctggaa aaattctc               48

SEQ ID NO: 59              moltype = DNA   length = 62
FEATURE                    Location/Qualifiers
source                     1..62
                           mol_type = other DNA
                           organism = synthetic construct
SEQUENCE: 59
ctttacgtga ggacatatgt atatcctcct tctactttt gagatttgcc aggatatcga   60
cc                                                                 62

SEQ ID NO: 60              moltype = DNA   length = 55
FEATURE                    Location/Qualifiers
source                     1..55
                           mol_type = other DNA
                           organism = synthetic construct
SEQUENCE: 60
gcaaatctca aaaagtagaa ggaggatata catatgtcct cacgtaaaga gcttg       55

SEQ ID NO: 61              moltype = DNA   length = 38
FEATURE                    Location/Qualifiers
source                     1..38
                           mol_type = other DNA
                           organism = synthetic construct
SEQUENCE: 61
ggggatcctc tagattacag cagttctttt gctttcgc                          38

SEQ ID NO: 62              moltype = DNA   length = 25
FEATURE                    Location/Qualifiers
source                     1..25
                           mol_type = other DNA
                           organism = synthetic construct
SEQUENCE: 62
gtaatctaga ggatccccgg gtacc                                        25

SEQ ID NO: 63              moltype = DNA   length = 49
FEATURE                    Location/Qualifiers
source                     1..49
                           mol_type = other DNA
                           organism = synthetic construct
SEQUENCE: 63
caatggatgt acgcatatgt atatcctcct tgtcgacctg caggcatgc              49

SEQ ID NO: 64              moltype = DNA   length = 29
FEATURE                    Location/Qualifiers
source                     1..29
                           mol_type = other DNA
                           organism = synthetic construct
SEQUENCE: 64
```

```
gtgaaaccag taacgttata cgatgtcgc                                          29

SEQ ID NO: 65           moltype = DNA  length = 19
FEATURE                 Location/Qualifiers
source                  1..19
                        mol_type = other DNA
                        organism = synthetic construct
SEQUENCE: 65
ctcactgccc gctttccag                                                     19

SEQ ID NO: 66           moltype = DNA  length = 18
FEATURE                 Location/Qualifiers
source                  1..18
                        mol_type = other DNA
                        organism = synthetic construct
SEQUENCE: 66
cttcaccgcc tggccctg                                                      18

SEQ ID NO: 67           moltype = DNA  length = 23
FEATURE                 Location/Qualifiers
source                  1..23
                        mol_type = other DNA
                        organism = synthetic construct
SEQUENCE: 67
cgcccggaag agagtcaatt cag                                                23

SEQ ID NO: 68           moltype = DNA  length = 594
FEATURE                 Location/Qualifiers
source                  1..594
                        mol_type = genomic DNA
                        organism = Escherichia coli
SEQUENCE: 68
atgaaactga tcgtcgggat gacaggggct accggtgcgc tcttggtgt ggcattactg         60
caagcgctgc gggagatgcc gaatgtcgag actcatctgg tgatgtcgaa gtgggcgaaa       120
accaccattg aactggaaac gccttacagc gcccgcgatg ttgctgccct cgctgacttc       180
agccataacc cggcggatca ggcggcgacc atctcctcag gttcctttcg tacagacggc       240
atgatcgtta ttccgtgcag tatgaaaacg ctcgccggta ccgcgctgg ttacgctgat        300
ggcctggtag ggcgcgcggc ggacgtcgtg cttaaagaag gccgcaaact ggtgctggtg       360
ccgcgtggaa tgccgcttag caccatccat ctcgaaaata tgctcgcact ttcacgcatg       420
ggcgtggcga tggtgccgcc gatgcctgcc ttttataacc atcccgaaac ggtagatgac       480
attgtccacc acgtggtagc ccgcgtgctg gatcaatttg gccttgaaca tccctacgcc       540
aggcgctggc aaggattgcc gcaggcccgg aattttctc aggagaatga ataa              594

SEQ ID NO: 69           moltype = DNA  length = 237
FEATURE                 Location/Qualifiers
source                  1..237
                        mol_type = genomic DNA
                        organism = Escherichia coli
SEQUENCE: 69
atgatttgtc cacgttgtgc cgatgaacag attgaagtga tggcgaaatc gccggtgaaa        60
gatgtcgtgg cggtatatca gtgccagcat tgcctttata cctggcgcga taccgaaccg       120
ctgcgccgta ccagccgcga acattatccc gaagcgttcc gcatgacgca gaaagatatt       180
gatgacgcgc caatggtgcc gagcatcccg ccgctgctgg cggaaggtaa gcgctaa          237

SEQ ID NO: 70           moltype = DNA  length = 28
FEATURE                 Location/Qualifiers
source                  1..28
                        mol_type = other DNA
                        organism = synthetic construct
SEQUENCE: 70
catatgaaac tgatcgtcgg gatgacag                                           28

SEQ ID NO: 71           moltype = DNA  length = 33
FEATURE                 Location/Qualifiers
source                  1..33
                        mol_type = other DNA
                        organism = synthetic construct
SEQUENCE: 71
cttttattca ttctcctgag aaaaattccg ggc                                     33

SEQ ID NO: 72           moltype = DNA  length = 56
FEATURE                 Location/Qualifiers
source                  1..56
                        mol_type = other DNA
                        organism = synthetic construct
SEQUENCE: 72
ttctcaggag aatgaataaa aggaggatat acatatgatt tgtccacgtt gtgccg            56

SEQ ID NO: 73           moltype = DNA  length = 23
```

```
FEATURE                 Location/Qualifiers
source                  1..23
                        mol_type = other DNA
                        organism = synthetic construct
SEQUENCE: 73
gattagcgct taccttccgc cag                                              23

SEQ ID NO: 74           moltype = DNA   length = 39
FEATURE                 Location/Qualifiers
source                  1..39
                        mol_type = other DNA
                        organism = synthetic construct
SEQUENCE: 74
ggaaggtaag cgctaatcta gagtcgacct gcaggcatg                             39

SEQ ID NO: 75           moltype = DNA   length = 59
FEATURE                 Location/Qualifiers
source                  1..59
                        mol_type = other DNA
                        organism = synthetic construct
SEQUENCE: 75
cgacgatcag tttcatatgt atatcctcct tttatttttgc gctaccctgg ttttttttcc     59

SEQ ID NO: 76           moltype = DNA   length = 1440
FEATURE                 Location/Qualifiers
source                  1..1440
                        mol_type = genomic DNA
                        organism = Pseudomonas putida
SEQUENCE: 76
atgagcaaga ttctcaccac cgccagcggt gcacctgtag ccgacaacca gaactcccgc      60
tccgccggcc cacgcggccc gctgctgctc gacgacttcc acctgatcga aagctcgcc     120
catttcaacc gtgagaacat ccccgagcgc cgggtacacg cgaagggttc gggcgcctat    180
ggcactttta ccgtaacccg cgacatcacc ggttacacca cgccaaaact gttcgagcag    240
gttggcaagc agaccgagac atttctgcgc ttctctaccg tgggtggcga acgtggttct    300
gcggacacag agcgagaccc tcgcggattt gccgttaagt tctacaccga ggaaggtaac    360
tgggacatcg tgggtaacaa cacgccagtg ttccttcattc gtgatccgct caagttcccg   420
gactttatcc acacccagaa acggcacccg cagtccaacc tgaaaaacgc ccaaatattt    480
tgggattcct ggtcgcactc gcccgaggcg ctgcaccaag tcaccatcct gttctctgat    540
cgtggcattc cggacggcta ccgccacatg cacggctttg gcagccacac ctacagccg    600
atcaatgccc agggtgagcg cacttgggtc aaatgcact tcaagaccca gcagggcatc    660
aagaaccttg ctccggcaga tgccgcacgt ttggcaggta ctgacccgga ctacgcccag   720
cgcgacctgt tcgaagccat tgagcgaggt gattacccac gctggactgt ctgcatccag    780
gtgatgagcg aagccgaagc cgcgaccgc gacgagaacc cgttcgacgt gaccaaaacc     840
tggtcacaaa aggactaccc gttgatcgaa gtgggcgtgc ttgagcttaa ccgtaacccg    900
ctcaattact cgccgaagt cgagcaggct gccttcgggc caagcaacat ggtgccgggg    960
gtcggcctgt cgcagaccg catgctccag ggtcgcgtat cgcctacgc ggacgcacac    1020
cgctaccgtg tgggtaccaa ccaccaacag ttgccggtga atgcgccacg ctgcccggtc   1080
aacagctacc agcgcgacgg ctccatggcc actggcagct atggcagtgc cgcgaactac   1140
gaaccaacaa ctacgccgc ggcaccgaag cagtcgccac gtcacgcaga gcccgcattg    1200
gccctgaatg gttcggccga ccgttacgat caccgcgagg acgctgacta ctacagccac    1260
gccggcgcgc tgttccgcct gatgagtgat gagcagaagg ccctgctgat cagcaacatc    1320
gctggaacca tggcgggtgt cagcgaaaac gtcatccaac ggcagttgca gtacttcttc    1380
aaggccgacc cagcctacgg agaaggcatc gccaagggcc tgggcatcaa tctcgcctaa   1440

SEQ ID NO: 77           moltype = DNA   length = 26
FEATURE                 Location/Qualifiers
source                  1..26
                        mol_type = other DNA
                        organism = synthetic construct
SEQUENCE: 77
catatgagca agattctcac caccgc                                           26

SEQ ID NO: 78           moltype = DNA   length = 25
FEATURE                 Location/Qualifiers
source                  1..25
                        mol_type = other DNA
                        organism = synthetic construct
SEQUENCE: 78
cttttaggcg agattgatgc ccagg                                            25

SEQ ID NO: 79           moltype = DNA   length = 42
FEATURE                 Location/Qualifiers
source                  1..42
                        mol_type = other DNA
                        organism = synthetic construct
SEQUENCE: 79
catcaatctc gcctaaaagg aggatataca tatgaccgca cc                         42

SEQ ID NO: 80           moltype = DNA   length = 59
```

```
FEATURE                 Location/Qualifiers
source                  1..59
                        mol_type = other DNA
                        organism = synthetic construct
SEQUENCE: 80
ggtgagaatc ttgctcatat gtatatcctc cttgagctcg aattcttctg tttcctgtg    59

SEQ ID NO: 81           moltype = DNA  length = 1053
FEATURE                 Location/Qualifiers
source                  1..1053
                        mol_type = genomic DNA
                        organism = Corynebacterium glutamicum
SEQUENCE: 81
atgaattatc agaacgacga tttacgcatc aaagaaatca aagagttact tcctcctgtc    60
gcattgctgg aaaaattccc cgctactgaa aatgccgcga atacggttgc ccatgcccga   120
aaagcgatcc ataagatcct gaaaggtaat gatgatcgcc tgttggttgt gattggccca   180
tgctcaattc atgatcctgt cgcggcaaaa gagtatgcca ctcgcttgct ggcgctgcgt   240
gaagagctga aagatgagct ggaaatcgta atgcgcgtct attttgaaaa gccgcgtacc   300
acggtgggct ggaaagggct gattaacgat ccgcatatgg ataatagctt ccagatcaac   360
gacggtctgc gtatagcccg taaattgctg cttgatatta cgacagcggt ctgccagcg   420
gcaggtgagt ttctcaatat gatcacccca caatatctcg ctgacctgat gagctgggc   480
gcaattggcg cacgtaccac cgaatcgcag gtgcaccgcg aactggcatc agggctttct   540
tgtccggtcg gcttcaaaaa tggcaccgac ggtacgatta agtggctat cgatgccatt   600
aatgccgccg gtgcgccgca ctgcttcctg tccgtaacga aatggggca ttcggcgatt   660
gtgaatacca gcggtaacgg cgattgccat atcattctgc gcggcggtaa agagcctaac   720
tacagcgcga agcacgttgc tgaagtgaaa gaagggctga acaaagcagg cctgccagca   780
caggtgatga tcgatttcag ccatgctaac tcgtccaaac aattcaaaaa gcagatggat   840
gtttgtgctg acgtttgcca gcagattgcc ggtggcgaaa aggccattat tggcgtgatg   900
gtggaaagcc atctggtgga aggcaatcag agcctcgaga gcggggagcc gctggcctac   960
ggtaagagca tcaccgatgc ctgcatcggc tgggaagata ccgatgctct gttacgtcaa  1020
ctggcgaatg cagtaaaagc gcgtcgcggg taa                               1053

SEQ ID NO: 82           moltype = DNA  length = 37
FEATURE                 Location/Qualifiers
source                  1..37
                        mol_type = other DNA
                        organism = synthetic construct
SEQUENCE: 82
catatgaatt atcagaacga cgatttacgc atcaaag                               37

SEQ ID NO: 83           moltype = DNA  length = 21
FEATURE                 Location/Qualifiers
source                  1..21
                        mol_type = other DNA
                        organism = synthetic construct
SEQUENCE: 83
cttttacccg cgacgcgctt t                                               21

SEQ ID NO: 84           moltype = DNA  length = 43
FEATURE                 Location/Qualifiers
source                  1..43
                        mol_type = other DNA
                        organism = synthetic construct
SEQUENCE: 84
cgtcgcgggt aaaaggagga tatacatatg tcctcacgta aag                       43

SEQ ID NO: 85           moltype = DNA  length = 64
FEATURE                 Location/Qualifiers
source                  1..64
                        mol_type = other DNA
                        organism = synthetic construct
SEQUENCE: 85
gtcgttctga taattcatat gtatatcctc cttctacttt ttgagatttg ccaggatatc    60
gacc                                                                  64
```

GENETIC ENGINEERING BACTERIUM FOR DE NOVO SYNTHESIS OF CIS,CIS-MUCONIC ACID BY TAKING GLUCOSE AS SUBSTRATE AND APPLICATIONS THEREOF

SEQUENCE LISTING

The substitute sequence listing is submitted as a XML file filed via EFS-Web, with a file name of "Substitute Sequence_Listing.XML", a creation date of Apr. 13, 2025, and a size of 96,906 bytes. The substitute sequence Listing filed via EFS-Web is a part of the specification and is incorporated in its entirety by reference herein.

TECHNICAL FIELD

The present invention relates to the technical field of genetic recombination and metabolic engineering, and more particularly relates to a genetic engineering bacterium for de novo synthesis of cis,cis-muconic acid by taking glucose as a substrate and applications thereof.

BACKGROUND cis,cis-muconic acid (MA) is a C6 compound of which two ends have two carboxy groups and the middle has two double bonds. It has a molecular formula of $C_6H_6O_4$ and a molecular weight of 142.11, is an industrial platform chemical compound for producing essential chemicals such as nylon-66, adipic acid and polyurethane, and is an important potential raw material for preparing functional resins, medicines and agricultural chemicals. Particularly the MA plays an important role in producing the adipic acid while serving as a raw material. Consumption of adipic acid has already exceeded 4 million tonnages all over the world; the consumption of the adipic acid also exceeds 1 million tonnages in China; and the quantity demanded is increasing with the development of economy. Traditional MA production is chemical synthesis, and mainly refers to production performed by utilizing nonrenewable petrochemical resource derivatives as raw materials through highly corrosive or irritating solvents such as peracetic acid and acetic acid. Such a method has high time consumption and great pollution, and mismatches with the goal of sustainable development in today's world. Therefore, developing an environment-friendly MA production method attracts more and more attentions. With the gradual maturity of genetic manipulation means and metabolic engineering technologies, the research focus of MA production has gradually approached to microbial conversion. A biological conversion method does not need any catalyst, solvent or oxidant, and is a clean and high-harmlessness production process. The biological conversion may effectively alleviate numerous adverse effects brought by chemical synthesis of the MA, but a concentration of the MA produced by a microbial method and production efficiency need to be further improved.

Different microbes have different endogenous metabolic properties, and mainly include two manners such as biological conversion of aromatic compounds and microbial fermentation of saccharides in the microbial conversion. For example, the microbes such as *Pseudomonas putida* and *Rhodococcus opacus* may metabolize some aromatic compounds through optimized expression of p-hydroxybenzoic acid-3-hydroxylase in strains; and MA of 40 g/L is produced in fed-batch fermentation by taking p-coumaric acid as a substrate (Kuatsjah E, et al. Debottlenecking 4-hydroxybenzoate hydroxylation in *Pseudomonas putida* KT2440 improves muconate productivity from p-coumarate). Vanillin dehydrogenase is introduced by knocking out vanillin dehydrogenase genes in *Rhodococcus opacus* by Jin Mingjie, et al., and MA of 4.3 g/L is obtained, thereby achieving conversion from the vanillin to the MA. (Jin, et al. Deciphering the metabolic distribution of vanillin in *Rhodococcus opacus* during lignin valorization). However, most of the benzene raw materials used in current production are derived from petroleum resources and belong to nonrenewable raw materials, while direct production of the MA by utilizing a simple carbon source such as glucose has more important significance to some extent. Most of the conventional model organisms such as *Saccharomyces cerevisiae* and *Escherichia coli* are modified to directly produce the MA by utilizing the glucose. In researches of Wang, et al., by changing shikimate pathway flux in Saccharomycetes and increasing phosphoenolpyruvate supply, production of MA of 20.8 g/L is achieved in a 10 L fermentation tank (Wang G, et al. An integrated yeast-based process for cis,cis-muconic acid production). However, *Corynebacterium glutamicum* is a microbe having high fermentation capacity, and has been applied to industrial production of amino acids such as L-glutamic acid and L-lysine. Moreover, metabolically, the MA is just an intermediate of the own β-ketoadipic acid pathway. The *Corynebacterium glutamicum* has the congenital advantage of producing the MA, and is an ideal host for MA production in a biosynthetic pathway. Since bulk chemicals have relatively low values, increasing the product concentration and synthetic efficiency is the key to reduce the cost. To facilitate more efficient production of a target product in a cell factory, production strains must be continuously optimized and modified to increase the target product conversion efficiency by continuously utilizing many means such as molecular biological techniques and fermentation control, thereby creating a possibility for efficient and low-cost production.

Therefore, providing a genetic engineering bacterium for de novo synthesis of cis,cis-muconic acid by taking glucose as a substrate and applications thereof is a problem that urgently needs to be solved by those skilled in the art.

SUMMARY

In view of this, the present invention provides a genetic engineering bacterium for de novo synthesis of cis,cis-muconic acid (MA) by taking glucose as a substrate and applications thereof. With respect to problems existing in de novo synthesis of MA in a current biological method, a biological pathway for efficient de novo synthesis of MA is developed, and a recombinant *Corynebacterium glutamicum* that can be used for producing the MA by more efficiently utilizing glucose is constructed.

To achieve the above purpose, the present invention adopts the following technical solution:

A genetic engineering bacterium for de novo synthesis of cis,cis-muconic acid by taking glucose as a substrate is provided. The genetic engineering bacterium is modified with chassis microbes, and includes recombinant *Corynebacterium glutamicum* for a cis,cis-muconic acid pathway construction module and an intermediate high-yield module.

Modification of the chassis microbes is as follows: the *Corynebacterium glutamicum* serves as an original strain; and pyk(cgl2089)(pyruvate kinase), aroE(cgl1835) (shikimate5-dehydrogenase), pcaG/H(cgl2630, cgl2631) (protocatechuate 3,4-dioxygenase subunit beta (pcaH), protocatechuate 3,4-dioxygenase subunit alpha (pcaG)), and catB (cgl2635) (chloromuconate cycloisomerase) genes are knocked out.

The cis,cis-muconic acid pathway construction module expresses protocatechuate decarboxylase genes, UbiX-like flavin prenyltransferase genes, 4-hydroxybenzoate decarboxylase, subunit D genes and catechol 1,2-dioxygenase genes.

The intermediate high-yield module expresses 3-dehydroquinate synthase genes, 3-dehydroquinate dehydratase genes, phosphate isomerase genes and transketolase genes.

Further, the protocatechuate decarboxylase genes are *Klebsiella Pneumoniae*-derived protocatechuate decarboxylase genes aroY.

The UbiX-like flavin prenyltransferase genes include *Escherichia coli*-derived UbiX-like flavin prenyltransferase genes kpdB, and *Klebsiella pneumoniae*-derived UbiX-like flavin prenyltransferase genes kpdB.

The 4-hydroxybenzoate decarboxylase, subunit D genes include *Escherichia coli*-derived 4-hydroxybenzoate decarboxylase, subunit D genes kpdD, and *Klebsiella pneumoniae*-derived 4-hydroxybenzoate decarboxylase, subunit D genes kpdD.

The catechol 1,2-dioxygenase genes include *Pseudomonas putida*-derived catechol 1,2-dioxygenase genes catA and *Corynebacterium glutamicum* endogenous catechol 1,2-dioxygenase genes catA.

The 3-dehydroquinate synthase is a *Corynebacterium glutamicum* endogenous 3-dehydroquinate synthase gene aroB.

The 3-dehydroquinate dehydratase genes are *Corynebacterium glutamicum* endogenous 3-dehydroquinate dehydratase genes aroD.

The phosphate isomerase genes are *Corynebacterium glutamicum* endogenous phosphate isomerase genes qsuB.

A nucleotide sequence of the *Klebsiella pneumoniae*-derived protocatechuate decarboxylase genes is shown as SEQ ID NO.37.

A nucleotide sequence of the *Escherichia coli*-derived UbiX-like flavin prenyltransferase genes kpdB is shown as SEQ ID NO.68.

A nucleotide sequence of the *Klebsiella pneumoniae*-derived UbiX-like flavin prenyltransferase genes kpdB is shown as SEQ ID NO.38.

A nucleotide sequence of the *Escherichia coli*-derived 4-hydroxybenzoate decarboxylase, subunit D genes kpdD is shown as SEQ ID NO.69.

A nucleotide sequence of the *Klebsiella pneumoniae*-derived 4-hydroxybenzoate decarboxylase, subunit D genes kpdD is shown as SEQ ID NO.39.

A nucleotide sequence of the *Pseudomonas putida*-derived catechol 1,2-dioxygenase genes catA is shown as SEQ ID NO.76.

A nucleotide sequence of the *Corynebacterium glutamicum* endogenous catechol 1,2-dioxygenase genes catA is shown as SEQ ID NO.35.

A nucleotide sequence of the *Corynebacterium glutamicum* endogenous 3-dehydroquinate synthase gene aroB is shown as SEQ ID NO.51.

A nucleotide sequence of the *Corynebacterium glutamicum* endogenous 3-dehydroquinate dehydratase genes aroD is shown as SEQ ID NO.52.

A nucleotide sequence of the *Corynebacterium glutamicum* endogenous phosphate isomerase genes qsuB is shown as SEQ ID NO.50.

A nucleotide sequence of the transketolase genes tkt is shown as SEQ ID NO.53.

Preferably, the protocatechuate decarboxylase genes are the *Klebsiella pneumoniae*-derived protocatechuate decarboxylase genes aroY.

The UbiX-like flavin prenyltransferase genes are the *Klebsiella pneumoniae*-derived UbiX-like flavin prenyltransferase genes kpdB.

The 4-hydroxybenzoate decarboxylase, subunit D genes are the *Klebsiella pneumoniae*-derived 4-hydroxybenzoate decarboxylase, subunit D genes kpdD.

The catechol 1,2-dioxygenase genes are the *Corynebacterium glutamicum* endogenous catechol 1,2-dioxygenase genes catA.

The 3-dehydroquinate synthase is the *Corynebacterium glutamicum* endogenous 3-dehydroquinate synthase gene aroB.

The 3-dehydroquinate dehydratase genes are the *Corynebacterium glutamicum* endogenous 3-dehydroquinate dehydratase genes aroD.

The phosphate isomerase genes are the *Corynebacterium glutamicum* endogenous phosphate isomerase genes qsuB.

Further, the intermediate high-yield module further expresses phospho-2-dehydro-3-deoxyheptonate aldolase genes.

A nucleotide sequence of the phospho-2-dehydro-3-deoxyheptonate aldolase genes is shown as SEQ ID NO.81.

Further, a construction method of a genetic engineering bacterium for de novo synthesis of cis,cis-muconic acid by taking glucose as a substrate includes the following steps:

(1) taking *Corynebacterium glutamicum* ATCC13032 as an original strain, and knocking out pyk(cgl2089), aroE (cgl1835), pcaG/H(cgl2630, cgl2631) and catB(cgl2635) genes to obtain modified *Corynebacterium glutamicum*; and (2) expressing the cis,cis-muconic acid pathway construction module and the intermediate high-yield module in the modified *Corynebacterium glutamicum*.

Further, the present invention provides an application of the genetic engineering bacterium or the method in production of cis,cis-muconic acid.

Further, the present invention provides an application of the genetic engineering bacterium or the method in yield increase of the cis,cis-muconic acid.

Further, the present invention provides a method for producing cis,cis-muconic acid, wherein fermentation is performed by utilizing the genetic engineering bacterium or a genetic engineering bacterium constructed by the method.

Thus, the present invention provides a biological pathway for synthesizing cis,cis-muconic acid (FIG. 1):

In the *Corynebacterium glutamicum*, 3 major decomposition pathways in a glucose production pathway are knocked out by virtue of chassis modification; and deletion in MA production with the glucose and low-activity enzyme genes and related proteins thereof are expressed, thereby enhancing key enzyme genes in a core pathway.

The major decomposition pathways in MA production with the glucose are as follows: aroE(cgl1835) (shikimate 5-dehydrogenase) is knocked out to decrease shikimate flux; pcaG/H(cgl2630, cgl2631) (protocatechuate 3,4-dioxygenase subunit beta (pcaH), protocatechuate 3,4-dioxygenase subunit alpha (pcaG)) are knocked out to block transformation to 3-carboxymuconic acid; catB(cgl2635) (chloromuconate cycloisomerase) is knocked out to block muconic acid from being decomposed into muconolactone; and the major decomposition pathways in MA production are knocked out, thereby obtaining higher flux in MA production and achieving higher enrichment of the MA.

The expression of the deletion in MA production with the glucose and low-activity enzyme genes and related proteins thereof is as follows: by expressing aroY (protocatechuate decarboxylase), kpdB (UbiX-like flavin prenyltransferase), kpdD (4-hydroxybenzoate decarboxylase, subunit D) and catA (catechol 1,2-dioxygenase) of different sources, the MA production pathway in the strain is constructed.

The enhancement of the key enzyme genes in the core pathway is as follows: by knocking out pyk(cgl2089) (pyruvate kinase) and expressing tkt (transketolase), accumulation of precursor substances phosphoenolpyruvate (PEP) and erythrose 4-phophate (E4P) synthesized by 3-deoxy-D-arabinoheptulosonate-7-phosphate (DAHP) in the shikimate pathway is respectively increased; and the flux in the production pathway is increased by increasing flux of the PEP and the E4P, thereby facilitating production of the MA.

The enhancement of the key enzyme genes in the core pathway is further as follows: endogenous aroG (phospho-2-dehydro-3-deoxyheptonate aldolase), aroB (3-dehydroquinate synthase), aroD (shikimate/quinate dehydratase) and qsuB (phosphate isomerase) are over-expressed by utilizing a combinational metabolic engineering strategy; and by virtue of over-expression of key intermediate production genes, an intermediate conversion degree is improved, thereby obtaining more MA accumulation.

Through the above technical solutions, compared with the prior art, the present invention provides the genetic engineering bacterium for de novo synthesis of cis,cis-muconic acid by taking glucose as the substrate and applications of the genetic engineering bacterium, and specifically provides a more efficient recombinant *Corynebacterium glutamicum* for production of MA by utilizing the glucose. By knocking out the major decomposition pathways in the production pathway and expressing the endogenous deletion of the strain and the low-activity enzyme genes and proteins thereof, the production pathway in the strain is constructed. Then, by increasing metabolic flux of the production pathway and enhancing the key enzyme genes in the core pathway, the production capacity of the strain is greatly improved; MA of 90.2 g/L is finally obtained in fermentation liquor and is the highest record of the MA produced by taking glucose or (and) glycerin as the substrate at present; and the product has wide application prospects. Moreover, possibilities are provided for green and low-cost production of numerous chemicals such as adipic acid and nylon-66.

DESCRIPTION OF DRAWINGS

To more clearly describe the technical solutions in the embodiments of the present invention or in the prior art, the drawings required to be used in the description of the embodiments or the prior art will be simply presented below. Obviously, the drawings in the following description are merely embodiments of the present invention, and for those ordinary skilled in the art, other drawings can also be obtained according to the provided drawings without contributing creative labor.

DETAILED DESCRIPTION

Figure 1:
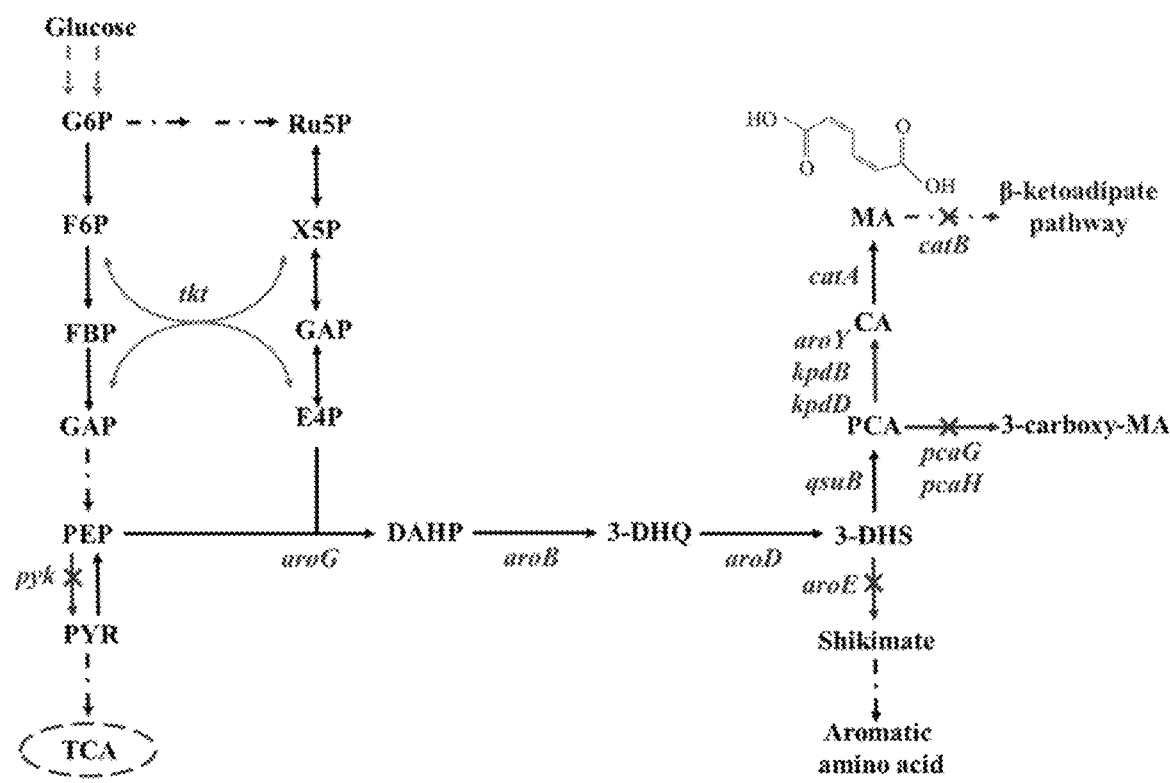
FIG. 1 is a biological synthesis pathway of cis,cis-muconic acid in the present invention.

Technical solutions in the embodiments of the present invention are described clearly and fully below in combination with the drawings in the embodiments of the present invention. Apparently, the described embodiments are merely part of the embodiments of the present invention, not all of the embodiments. Based on the embodiments in the present invention, all other embodiments obtained by those ordinary skilled in the art without contributing creative labor will belong to the protection scope of the present invention.

LBHIS medium: 5.0 g/L of peptone, 2.5 g/L of yeast powder, 5.0 g/L of NaCl, 18.5 g/L of brain heart infusion (BHI) and 91.0 g/L of sorbitol. 1.8-2% of agar is added into a corresponding LBHIS solid medium.

LBG medium: 10.0 g/L of peptone, 5.0 g/L of yeast powder, 10.0 g/L of NaCl and 20.0 g/L of glucose.

EPO medium: 10.0 g/L of peptone, 5.0 g/L of yeast powder, 10.0 g/L of NaCl, 30.0 g/L of glycine and 10.0 g/L of Tween80.

30% sucrose medium: 10.0 g/L of peptone, 5.0 g/L of yeast powder, 10.0 g/L of NaCl and 300.0 g/L of sucrose.

20% sucrose solid medium: 10.0 g/L of peptone, 5.0 g/L of yeast powder, 10.0 g/L of NaCl, 200.0 g/L of sucrose and 15.0 g/L of agar.

Fermentation medium: 65.0 g/L of glucose, 5.0 g/L of urea, 8.0 g/L of corn extract powder, $4\times10^{-4}$ g/L of biotin, $4\times10^{-4}$ g/L of $VB_1$ biotin, 1.0 g/L of $K_2HPO_4$, 1.0 g/L of $KH_2PO_4$, 29.4 mg/L of $CaCl_2 \cdot 2H_2O$, 1.2325 g/L of $MgSO_4 \cdot 7H_2O$ and 0.2% of a trace element solution. (a preparation method of the trace element solution includes steps: weighing 1 g of $FeSO_4 \cdot 7H_2O$, 1 g of $MnSO_4 \cdot H_2O$, 0.1 g of $ZnSO_4 \cdot 7H_2O$, 0.2 g of $CuSO_4$ and 0.002 g of $NiCl_2 \cdot 6H_2O$, adding water to obtain a fixed volume of 100 mL; then adding 100 μl of concentrated hydrochloric acid to regulate the pH value; filtering the bacterium with a filtration membrane; and adding 0.2% into a fermentation medium system.)

Embodiment 1

A construction method of a genetic engineering bacterium for de novo synthesis of cis,cis-muconic acid by taking glucose as a substrate includes the following steps:

(1) Genome DNA of *Corynebacterium glutamicum* ATCC13032 was taken as a template; catB-up was amplified by using a primer catB-up-F/catB-up-R (as shown in SEQ ID NO.1); and catB-down was amplified by using a primer catB-down-F/catB-down-R (as shown in SEQ ID NO.2), so as to obtain upstream and downstream homologous arms of which the catB was knocked out. Primer sequences were as follows:

```
catB-up-F:
                                    SEQ ID NO. 3
5'-CTAGACTTTTTCCAGAGCTTTTTGGAACAGCTTG-3';;
```

-continued catB-up-R:
SEQ ID NO. 4
5'-CCAGAAAGCCATAGAAAAAGGAGAATTATCGATGCTGTTTC
TAGCACG-3';;

catB-down-F:
SEQ ID NO. 5
5'-TTTTTCTATGGCTTTCTGGTTAAGTGGGAAA-3';;

catB-down-R:
SEQ ID NO. 6
5'-TTATCGAGTTCAGCCGATCACAAAGATTTTTC-3';.

Gene amplification system: 25 µL of Primestar (Takara), 2 µL of a forward primer, 2 µL of a reverse primer, 1 µL of a template and 20 µL of ddH$_2$O.

Gene amplification procedures: pre-denaturation at 98° C. for 3 minutes; denaturation at 98° C. for 10 seconds; annealing at 57° C. for 30 seconds; extension at 72° C. by 10 s/kb, totaling 35 cycles; and extension at 72° C. for 10 minutes.

The PCR product was subjected to agarose gel electrophoresis and product recovery to obtain gene segments catB-up and catB-down.

A plasmid vector pk18mobsacb was linearized with a primer pK18-catBF/pK18-catBR to obtain a vector pk-catB, wherein primer sequences were as follows:

pK18-catBF:
SEQ ID NO. 7
5'-ATCGGCTGAACTCGATAAAAGCTTGGCACTGGCCG-3';;

pK18-catBR:
SEQ ID NO. 8
5'-CAAAAAGCTCTGGAAAAAGTCTAGAGGATCCCCGGGTACCG-3';.

3 µL of catB-up, 3 µL of catB-down, 4 µL of a vector pK-catB and 10 µL of Gibson ligase were added into a PCR tube, wherein a ligation temperature was 50° C.; ligation time was 15 min; and a total volume of the system was 20 µL.

The total 20 µL Gibson-ligated ligation system was transformed into *E. coli* Trans10 commercial competent cells (TransGen Biotech) for culture and retention. The transformation process was strictly operated according to the instructions as follows: after cultured at 37° C. for 1 h, the ligation system was coated onto an LB plate (containing 50 µg/mL of kanamycin); then the system was cultured at 37° C. for 12 h; and 10-20 single colonies were selected to perform PCR amplification and DNA sequencing verification. A primer used in PCR amplification and DNA sequencing verification was the above catB-up-F/catB-down-R.

An accurate single colony was selected and then named as *Escherichia coli* EC001; a plasmid was named as pK18-catB and subjected to expanding propagation to perform plasmid extraction so as to obtain a plasmid pK18-catB; and then the plasmid was electro-transformed into *Corynebacterium glutamicum* ATCC13032 competent cells.

Preparation of the *Corynebacterium glutamicum* ATCC13032 competent cells was as follows: a glycerin-preserved strain of *Corynebacterium glutamicum* ATCC13032 was subjected to streak inoculation on an LBHIS plate; the strain was cultured in an incubator at 30° C. until the colony was clear; the colony was picked from the plate and inoculated into an LBHIS test-tube fluid medium for culture for 12 h; then the culture solution was inoculated into an EPO medium at an initial OD$_{600}$ of about 0.3; the solution was continuously cultured until the OD$_{600}$ was 0.9; the bacterium solution was added into a centrifuge tube; the centrifuge tube was placed in an ice bath for 15 min; the bacterium solution was frozen and centrifuged at 4500 rpm for 10 min to collect the thallus (separately filled in 1.5 mL centrifuge tubes); the thallus was resuspended with 100 µL of pre-cooled 10% glycerin; the above centrifugation was continuously repeated for three times; and the thallus was resuspended with 100 µL of 10% sterile glycerin after washing completion, thereby obtaining the *Corynebacterium glutamicum* ATCC13032 competent cells.

The electrotransformation method was as follows: 2-4 µL of the plasmid was added into competent cells of each tube and placed in an ice bath for 10 min; the mixed solution was transferred into a pre-cooled electric shock cup, and electric shock was conducted under conditions of 1.8 kv, an electric shock rate of 5 ms, 50 µF and 100Ω; a 800 µL LBHIS medium was immediately added after electric shock completion; then the solution was placed in a water bath at 46° C. for 6 min and then cultured at 30° C. for 2-3 h; the solution was coated on a solid LBHIS plate containing 50 µg/mL kanamycin; and the solution was cultured at 30° C. for 24-36 h for verification.

For a gene knockout strain, several single colonies growing on the above plate needed to be subjected to sacB gene verification, wherein verification primers were as follows:

sacB-F:
SEQ ID NO. 9
5'-CTCAAGCGTTTGCGAAAGAAACG-3';;

sacB-R:
SEQ ID NO. 10
5'-GAGTCAGTGAACAGGTACCATTTGCC-3';.

The accurately verified strain was inoculated into a 30% sucrose medium to be cultured for 24 h; after the bacterium solution was turbid, the strain was subjected to streak culture on a 20% sucrose medium; colony PCR of the sacB gene was continuously performed; then a single colony in which the sacB gene was not amplified was the accurate colony; the thallus was inoculated into an LBHIS fluid medium for culture; the thallus was purified on an LBHIS solid plate after the solution was turbid; and verification was performed by using forward and reverse primers catB-up-F/catB-up-R and catB-down-F/catB-down-R of the target gene. After confirmed, the strain was the target gene knockout strain and may be preserved for later use. The strain was named as *Corynebacterium glutamicum* GM1.

(2) Genome DNA of *Corynebacterium glutamicum* ATCC13032 was taken as a template; aroE-up was amplified by using a primer aroE-up-F/aroE-up-R (as shown in SEQ ID NO.11); and aroE-down was amplified by using a primer aroE-down-F/aroE-down-R (as shown in SEQ ID NO.12), so as to obtain upstream and downstream homologous arms of which the aroE was knocked out. Primer sequences were as follows:

aroE-up-F:
SEQ ID NO. 13
5'-GTCGCTCACCGCGATTTTAGAGTGGC-3';;

aroE-up-R:
SEQ ID NO. 14
5'-GATGTGACTAAATCTTAGTGACTATTTACATGGGTGG-3';;

aroE-down-F:
SEQ ID NO. 15
5'-GTCACTAAGATTTAGTCACATCCGAGAGCCGAGTACCG-3';;

aroE-down-R:
SEQ ID NO. 16
5'-TCTCTGCTTGAGACTTAAGCGTTATCCG-3';.

A plasmid vector pk18mobsacb was linearized with a primer pK18-aroEF/pK18-aroER to obtain a vector pk-aroE, wherein primer sequences were as follows:

pK18-aroEF:
SEQ ID NO. 17
5'-CTTAAGTCTCAAGCAGAGAGACCTGCAGGCATGCAAGC-3';;

pK18-aroER:
SEQ ID NO. 18
5'-TAAAATCGCGGTGAGCGACTCTAGAGGATCCCCGGGTAC-3';.

The gene amplification system and gene amplification procedures were the same as above; vectors aroE-up, aroE-down and pK-aroE were obtained; ligation and transformation verification manners were the same as above; *Escherichia coli* EC002 was obtained; the plasmid was named as pK18-aroE; and through expanding propagation, the plasmid was extracted to obtain a plasmid pK18-aroE.

The plasmid pK18-aroE was electro-transformed into *Corynebacterium glutamicum* GM1 competent cells. Preparation of the competent cells, electro-transformation, sacB verification and culture of the sucrose medium were the same as above. The aroE knockout verification primer was the above aroE-up-F/aroE-down-R.

Through verification of the verification primer, a strain of which the aroE was successfully knocked out was inoculated into an LBHIS fluid medium for culture; and the strain was subjected to streak culture on an LBHIS solid medium plate for purification and re-verification. After confirmed, the strain may be preserved for later use, and was named as *Corynebacterium glutamicum* GM2.

(3) Genome DNA of *Corynebacterium glutamicum* ATCC13032 was taken as a template; pcaG/H-up was amplified by using a primer pcaG/H-up-F/pcaG/H-up-R (as shown in SEQ ID NO.19); and pcaG/H-down was amplified by using a primer pcaG/H-down-F/pcaG/H-down-R (as shown in SEQ ID NO.20), so as to obtain upstream and downstream homologous arms of which the pcaG/H was knocked out. Primer sequences were as follows:

pcaG/H-up-F:
SEQ ID NO. 21
5'-AACGTTGACGGTGATGCCATC-3';;

pcaG/H-up-R:
SEQ ID NO. 22
5'-ATTGACCCGATCTTTATACTCCGACCTTG-3';;

pcaG/H-down-F:
SEQ ID NO. 23
5'-GAGTATAAAGATCGGGTCAATGCGAGACCTTTCT

GCGTCTAGTG-3';;

pcaG/H-down-R:
SEQ ID NO. 24
5'-CCATCGCATTGCCGAAAAGCTG-3';.

A plasmid vector pk18mobsacb was linearized with a primer pK18-pcaF/pK18-pcaR to obtain a vector pk-pca, wherein primer sequences were as follows:

pK18-pcaF:
SEQ ID NO. 25
5'-TTCGGCAATGCGATGGGACCTGCAGGCATGCAAGC-3';;

pK18-pcaR:
SEQ ID NO. 26
5'-ATCACCGTCAACGTTGACTCTAGAGGATC-3';.

The gene amplification system and gene amplification procedures were the same as above; vectors pcaG/H-up, pcaG/H-down and pk-pca were obtained; ligation and transformation verification manners were the same as above; *Escherichia coli* EC003 was obtained; the plasmid was named as pK18-pca; and through expanding propagation, the plasmid was extracted to obtain a plasmid pK18-pca.

The plasmid pK18-pca was electro-transformed into *Corynebacterium glutamicum* GM2 competent cells. Preparation of the competent cells, electro-transformation, sacB verification and culture of the sucrose medium were the same as above. The pcaG/H knockout verification primer was the above pcaG/H-up-F/pcaG/H-down-R.

Through verification of the verification primer, a strain of which the pcaG/H was successfully knocked out was inoculated into an LBHIS fluid medium for culture; and the strain was subjected to streak culture on an LBHIS solid medium plate for purification and re-verification. After confirmed, the strain may be preserved for later use, and was named as *Corynebacterium glutamicum* GM3.

(4) Genome DNA of *Corynebacterium glutamicum* ATCC13032 was taken as a template; pyk-up was amplified by using a primer pyk-up-F/pyk-up-R (as shown in SEQ ID NO.27); and pyk-down was amplified by using a primer pyk-down-F/pyk-down-R (as shown in SEQ ID NO.28), so as to obtain upstream and downstream homologous arms of which the pyk was knocked out. Primer sequences were as follows:

pyk-up-F:
SEQ ID NO. 29
5'-CTCTAGAGTCCAACAGAGGTGCCGTTGTCAAAG-3';;

pyk-up-R:
SEQ ID NO. 30
5'-GGCTCGCTTAAATCTTTCAAAAAATGCGTTGACAC-3';;

pyk-down-F:
SEQ ID NO. 31
5'-GAAAGATTTAAGCGAGCCCATAAGCCTAGTACGTCATTCC-3';;

pyk-down-R:
SEQ ID NO. 32
5'-CAGGTCGTCCTTGATGCAGCGATCGTG-3';.

A plasmid vector pk18mobsacb was linearized with a primer pK18-pykF/pK18-pykR to obtain a vector pk-pyk, wherein primer sequences were as follows:

pK18-pykF:
SEQ ID NO. 33
5'-CATCAAGGACGACCTGCAGGCATGCAAGC-3';;

pK18-pykR:
SEQ ID NO. 34
5'-CTCTGTTGGACTCTAGAGGATCCCCGGGTAC-3';.

The gene amplification system and gene amplification procedures were the same as above; vectors pyk-up, pyk-down and pk-pyk were obtained; ligation and transformation verification manners were the same as above; *Escherichia coli* EC004 was obtained; the plasmid was named as pK18- pyk; and through expanding propagation, the plasmid was extracted to obtain a plasmid pK18-pyk.

The plasmid pK18-pyk was electro-transformed into *Corynebacterium glutamicum* GM3 competent cells. Preparation of the competent cells, electro-transformation, sacB verification and culture of the sucrose medium were the same as above. The pyk knockout verification primer was the above pyk-up-F/pyk-down-R.

Through verification of the verification primer, a strain of which the pyk was successfully knocked out was inoculated into an LBHIS fluid medium for culture; and the strain was subjected to streak culture on an LBHIS solid medium plate for purification and re-verification. After confirmed, the strain may be preserved for later use, and was named as *Corynebacterium glutamicum* GM4.

(5) Genome DNA of *Corynebacterium glutamicum* ATCC13032 was taken as a template; the segment catA was amplified by using a primer CG-catA-F/CG-catA-R (as shown in SEQ ID NO.35); and *Corynebacterium glutamicum* derived catA with seamless cloning homologous arms (ribosome bind sites, as shown in SEQ ID NO.36) ligated with the plasmid was obtained.

Genome DNA of *Kleber pneumonia* subspecies was taken as a template; the segment aroY was amplified by using a primer aroY-F/aroY-R (as shown in SEQ ID NO.37); and a *Kleber pneumonia*-derived aroY segment with seamless cloning homologous arms in ligation with the catA and with RBS was obtained.

Genome DNA of *Kleber pneumonia* subspecies was taken as a template; the segment kpdB was amplified by using a primer KP-kpdB-F/KP-kpdB-R (as shown in SEQ ID NO.38); and a *Kleber pneumonia*-derived kpdB segment with seamless cloning homologous arms in ligation with the aroY was obtained.

Genome DNA of *Kleber pneumonia* subspecies was taken as a template; the segment kpdD was amplified by using a primer KP-kpdD-F/KP-kpdD-R (as shown in SEQ ID NO.39); and a *Kleber pneumonia*-derived kpdD segment with seamless cloning homologous arms in ligation with the kpdB and the plasmid and with RBS was obtained.

Primer sequences are as follows:

```
CG-catA-F:
                                         SEQ ID NO. 40
5'-CATATGACTTCAGCTGAACAGATCGTTGATC-3';;

CG-catA-R:
                                         SEQ ID NO. 41
5'-CTAGTCTTCCTTATCCAGGACGAATGGG-3';;

aroY-F:
                                         SEQ ID NO. 42
5'-CCTGGATAAGGAAGACTAGAAGGAGGATATACATATGACCGCA

CCGATTCAGGATC-3';;

aroY-R:
                                         SEQ ID NO. 43
5'-ATCCCAATAATCAGTTTCATATGTATATCCTCCTTTTATTTTGCG

CTACCCTGGTTTTTTTCC-3';;

KP-kpdB-F:
                                         SEQ ID NO. 44
5'-CATATGAAACTGATTATTGGGATGACGGGG-3';;

KP-kpdB-R:
                                         SEQ ID NO. 45
5'-TTATTCGATCTCCTGTGCAAATTGTTCT-3';;

KP-kpdD-F:
                                         SEQ ID NO. 46
5'-GCACAGGAGATCGAATAAAAGGAGGATATACATATGATTT

GTCCACGTTGCGC-3';;

KP-kpdD-R:
                                         SEQ ID NO. 47
5'-GATTAACGCTTATCTTCCGGCAATAGCG-3';.
```

A plasmid vector pEC-XK99E was linearized with a primer PEC-1-1F/PEC-1-1R to obtain a vector PEC, wherein primer sequences were as follows:

```
PEC-1-1F:
                                         SEQ ID NO. 48
5'-CGGAAGATAAGCGTTAATCTAGAGTCGACCTGCAGGCATG-3';;

PEC-1-1R:
                                         SEQ ID NO. 49
5'-GTTCAGCTGAAGTCATATGTATATCCTCCTTGAGCTCGAAT

TCTTCTGTTTCCTGTG-3';.
```

The gene amplification system and gene amplification procedures were the same as above; vectors catA, aroY, kpdB, kpdD and pEC-1 were obtained; and 1.5 μl of catA, 1.5 μl of aroY, 1.5 μl of kpdB, 1.5 μl of kpdD and 4 μl of pEC of different sources and 10 μl of Gibson ligase were added into PCR tubes. Ligation and transformation manners were the same as above; several selected colonies were sent to BGI Genomics Co., Ltd. for sequencing; the sequencing primer was the above CG-catA-F/KP-kpdBD-R; a sequencing manner was throughput sequencing; an accurate strain was named as *Escherichia coli* EC005; the plasmid was named as pEC-1; and through expanding propagation, the plasmid was extracted to obtain a plasmid pEC-1.

(6) Genome DNA of *Corynebacterium glutamicum* ATCC13032 was taken as a template; the segment qsuB was amplified by using a primer qsuB-F/qsuB-R (as shown in SEQ ID NO.50); and *Corynebacterium glutamicum*-derived qsuB with seamless cloning homologous arms in ligation with the plasmid was obtained.

Genome DNA of *Corynebacterium glutamicum* ATCC13032 was taken as a template; the segment aroB was amplified by using a primer aroB-F/aroB-R (as shown in SEQ ID NO.51); and a *Corynebacterium glutamicum*-derived aroB segment with seamless cloning homologous arms in ligation with the qsuB and with RBS was obtained.

Genome DNA of *Corynebacterium glutamicum* ATCC13032 was taken as a template; the segment aroD was amplified by using a primer aroD-F/aroD-R (as shown in SEQ ID NO.52); and a *Corynebacterium glutamicum*-derived aroD segment with seamless cloning homologous arms in ligation with the aroB and with RBS was obtained.

Genome DNA of *Escherichia coli* K-12 was taken as a template; the segment tkt was amplified by using a primer tkt-F/tkt-R (as shown in SEQ ID NO.53); and a *Corynebacterium glutamicum*-derived tkt segment with seamless cloning homologous arms in ligation with the aroD and the plasmid and with RBS was obtained.

Primer sequences were as follows:

```
qsuB-F:
                                         SEQ ID NO. 54
5'-CATATGCGTACATCCATTGCCACTG-3';;
```

-continued qsuB-R:
SEQ ID NO. 55
5'-CTAGTTTGGGATTCCCCGCTCG-3';;

aroB-F:
SEQ ID NO. 56
5'-GGGGAATCCCAAACTAGAAGGAGGATATACATATGAGCGCAG

TGCAGATTTTCAAC-3';;

aroB-R:
SEQ ID NO. 57
5'-CTTTTAGTGGCTGATTGCCTCATAAGC-3';;

aroD-F:
SEQ ID NO. 58
5'-GCAATCAGCCACTAAAAGGAGGATATACATATGCCTGGAAAA

ATTCTC-3';;

aroD-R:
SEQ ID NO. 59
5'-CTTTACGTGAGGACATATGTATATCCTCCTTCTACTTTTTGAGA

TTTGCCAGGATATCGACC-3';;

tkt-F:
SEQ ID NO. 60
5'-GCAAATCTCAAAAAGTAGAAGGAGGATATACATATGTCCTCACG

TAAAGAGCTTG-3';;

tkt-R:
SEQ ID NO. 61
5'-GGGGATCCTCTAGATTACAGCAGTTCTTTTGCTTTCGC-3';.

A plasmid vector PXMJ19 was linearized with a primer PXM-1-1F/PXM-1-1R to obtain a vector PXM, wherein primer sequences were as follows:

PXM-1-1F:
SEQ ID NO. 62
5'-GTAATCTAGAGGATCCCCGGGTACC-3';;

PXM-1-1R:
SEQ ID NO. 63
5'-CAATGGATGTACGCATATGTATATCCTCCTTGTCGACCTGCA

GGCATGC-3';.

The gene amplification system and gene amplification procedures were the same as above; vectors qsuB, aroB, aroD, tkt and PXM were obtained; and 1.5 µl of qsuB, 1.5 µl of aroB, 1.5 µl of aroD, 1.5 µl of tkt and 4 µl of PXM of different sources and 10 µl of Gibson ligase were added into PCR tubes. Ligation and transformation manners were the same as above; several selected colonies were sent to BGI Genomics Co., Ltd. for sequencing; the sequencing primer was the above qsuB-F/tkt-R; a sequencing manner was throughput sequencing; an accurate strain was named as *Escherichia coli* EC006; the plasmid was named as pXM-1; and through expanding propagation, the plasmid was extracted to obtain a plasmid pXM-1.

The plasmids pEC-1 and pXM-1 were simultaneously electro-transformed into *Corynebacterium glutamicum* GM4 competent cells, and experimental steps were the same as above. The cells were uniformly mixed and coated onto an LBHIS solid medium plate containing 50 g/L of kanamycin and 5 g/L of chloromycetin; after the colonies grew, single colonies growing on the plate were selected to verify kana (primer kana-F/kana-R) and Cm (primer Cm-F/Cm-R) genes; and a strain of which the two genes were verified accurate was named as *Corynebacterium glutamicum* MA1.

Primer sequences were as follows:

kana-F:
SEQ ID NO. 64
5'-GTGAAACCAGTAACGTTATACGATGTCGC-3';;

kana-R:
SEQ ID NO. 65
5'-CTCACTGCCCGCTTTCCAG-3';;

Cm-F:
SEQ ID NO. 66
5'-CTTCACCGCCTGGCCCTG-3';;

Cm-R:
SEQ ID NO. 67
5'-CGCCCGGAAGAGAGTCAATTCAG-3';.

The *Corynebacterium glutamicum* MA1 was respectively subjected to shaking flask fermentation in a 50 mL system and fermentation tank feed verification in a 5 L system.

①Strain Activation

Single colonies of the *Corynebacterium glutamicum* MA1 were selected to be inoculated into an LBHIS fluid medium and cultured at 30° C. at 200 rpm for 12 h; and then the colonies were transferred into a fresh LBG fluid medium for secondary activation for 12 h, wherein the activated strain MA1 was used for growth test or fermentation.

②Conditions of Shaking Flask Fermentation

Conditions of a constant temperature shaker were 30° C. and 200 rpm. 50 mL fermentation liquor (a fermentation medium contained 50 µg/mL of kanamycin and 5 µg/mL of chloromycetin) was filled in a 250 mL baffled flask; initial $OD_{600}$ of inoculation was 0.5; three parallel experiments were conducted for each strain; an inducer IPTG (having a final concentration of 0.8 mM) was added within 3 h after fermentation; and changes in saccharide components and fermentation products were detected by an HPLC method.

③Fermentation Conditions of a 5 L Fermentation Tank

Conditions of the fermentation tank were 30° C. and 400 rpm. An initial pH value was 7.0. $OD_{600}$ of inoculation was 2.0 (an inoculation dose was about 5-10% of a fermentation volume). Aeration was conducted at 0.2 L/min. A filling volume of the fermentation tank was 50% of the total volume. An appropriate amount of a defoaming agent was added during initial fermentation. Whether the defoaming agent needed to be added was determined according to the fermentation conditions. The pH value was automatically regulated with 50% phosphoric acid and 25% ammonia water respectively during fermentation. An inducer IPTG (having a final concentration of 0.8 mM) was added within 12 h after fermentation; glucose (having a glucose concentration of 800 g/L) was automatically fed at a rate of 5 mL/h within 24 h after fermentation; and changes in saccharide components and fermentation products were detected by an HPLC method.

Figure 2:
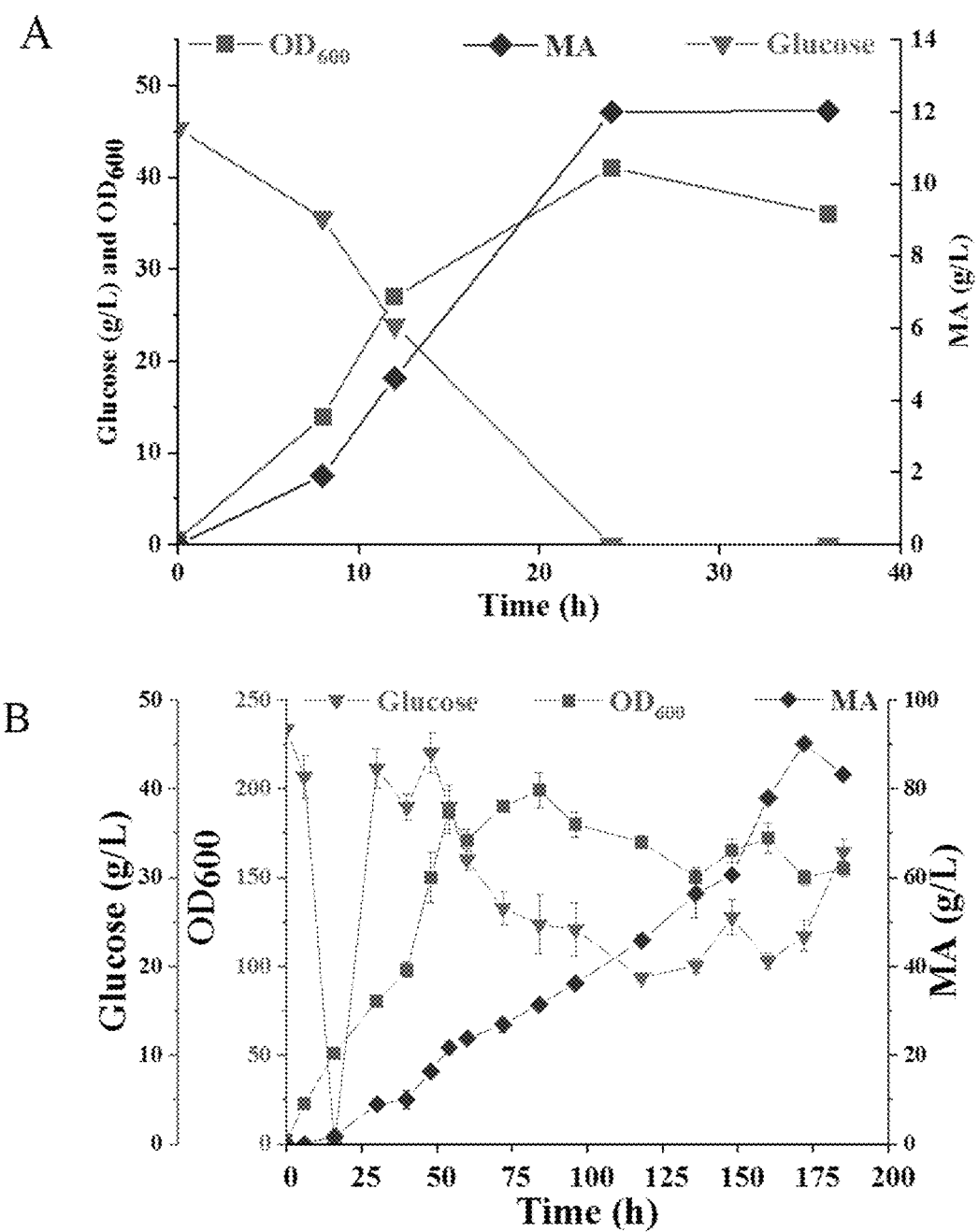
FIG. 2 shows growth and metabolism of a strain MA1 in fermentation of different systems and MA production situations in the present invention, wherein A: a fermentation system in a 50 mL shaking flask; B: a fermentation system in a 5 L fermentation tank.

Fermentation Product Detection:

A liquid mass spectrometer was purchased from Agilent Technologies. The glucose was detected by a chromatographic column Aminex HPX-87H column; a differential detector UltiMate 3000 Variable Wavelength Detector was used; a mobile phase was 5 mM $H_2SO_4$; a column temperature was 65° C.; and a flow rate was 0.6 mL/min. The MA was detected by a chromatographic column Aminex HPX-87H column; a mobile phase was 5 mM $H_2SO_4$; an ultraviolet detector RefractoMax 520 was used; a wavelength of the ultraviolet light was 210 nm; a column temperature was 40° C.; and a flow rate was 0.5 mL/min. Data peak maps of different fermentation samples were subjected to content calculation according to a standard curve drawn from the standard sample, and results were shown as Table 1, Table 2 and FIG. 2.

TABLE 1

Shaking flask fermentation of a 50 mL system

| Time (h) | OD$_{600}$ | Glucose (g/L) | MA (g/L) |
|---|---|---|---|
| 0 | 0.50 | 45.30 | 0.00 |
| 8 | 13.90 | 35.61 | 1.91 |
| 12 | 27.00 | 23.90 | 4.63 |
| 24 | 41.05 | 0.00 | 11.99 |
| 36 | 36.05 | 0.00 | 12.04 |

TABLE 2

Fermentation tank feed experiment of a 5 L system

| Time (h) | OD$_{600}$ | Glucose (g/L) | MA (g/L) |
|---|---|---|---|
| 0 | 2.50 | 46.73 | 0.00 |
| 6 | 22.50 | 41.35 | 0.03 |
| 16 | 50.90 | 0.00 | 1.68 |
| 30 | 80.50 | 42.30 | 9.00 |
| 40 | 98.00 | 37.94 | 10.01 |
| 48 | 150.00 | 44.05 | 16.40 |
| 54 | 187.00 | 37.92 | 21.66 |
| 60 | 171.00 | 32.03 | 23.77 |
| 72 | 190.00 | 26.55 | 26.90 |
| 84 | 199.00 | 24.74 | 31.42 |
| 96 | 180.00 | 24.16 | 36.12 |
| 118 | 170.00 | 18.73 | 45.85 |
| 136 | 150.00 | 20.08 | 56.31 |
| 148 | 165.00 | 25.54 | 60.59 |
| 160 | 172.00 | 20.62 | 77.91 |
| 172 | 150.00 | 23.41 | 90.20 |
| 185 | 155.00 | 32.88 | 83.20 |

In the shaking flask fermentation of the 50 mL system, MA of 12.04 g/L was produced by the strain (FIG. 2A); and in the fermentation tank feed experiment of the 5 L system, MA of 90.2 g/L was produced by the strain (FIG. 2B).

Embodiment 2

A construction method of a genetic engineering bacterium for de novo synthesis of cis,cis-muconic acid by taking glucose as a substrate includes the following steps:

Genome DNA of *Escherichia coli* EC869 was taken as a template; the segment kpdB was amplified by using a primer EC-kpdB-F/EC-kpdB-R (as shown in SEQ ID NO.68); and an *Escherichia coli* EC869-derived kpdB segment with seamless cloning homologous arms in ligation with the plasmid was obtained.

Genome DNA of *Escherichia coli* EC869 was taken as a template; the segment kpdD was amplified by using a primer EC-kpdD-F/EC-kpdD-R (as shown in SEQ ID NO.69); and a *Corynebacterium glutamicum*-derived kpdD segment with seamless cloning homologous arms in ligation with kpdB and the plasmid and with RBS was obtained.

Primer sequences were as follows:

```
EC-kpdB-F:
                                     SEQ ID NO. 70
5'-CATATGAAACTGATCGTCGGGATGACAG-3';;

EC-kpdB-R:
                                     SEQ ID NO. 71
5'-CTTTTATTCATTCTCCTGAGAAAAATTCCGGGC-3';;

EC-kpdD-F:
                                     SEQ ID NO. 72
5'-TTCTCAGGAGAATGAATAAAAGGAGGATATACATATGATTT

GTCCACGTTGTGCCG-3';;

EC-kpdD-R:
                                     SEQ ID NO. 73
5'-GATTAGCGCTTACCTTCCGCCAG-3';.
```

A plasmid vector pEC-1 was linearized with a primer PEC-2-1F/PEC-2-1R to obtain a vector PECa, wherein primer sequences were as follows:

```
PEC-2-1F:
                                     SEQ ID NO. 74
5'-GGAAGGTAAGCGCTAATCTAGAGTCGACCTGCAGGCATG-3';;

PEC-2-1R:
                                     SEQ ID NO. 75
5'-CGACGATCAGTTTCATATGTATATCCTCCTTTTATTTTGCGCT

ACCCTGGTTTTTTTCC-3';.
```

The gene amplification system and gene amplification procedures were the same as embodiment 1; vectors kpdB, kpdD and PECa were obtained; and 2 μl of kpdB, 2 μl of kpdD and 6 μl of PECa of different sources and 10 μl of Gibson ligase were added into PCR tubes. Ligation and transformation manners were the same as embodiment 1; several selected colonies were sent to BGI Genomics Co., Ltd. for sequencing; the sequencing primer was the above EC-kpdB-F/EC-kpdD-R; a sequencing manner was throughput sequencing; an accurate strain was named as *Escherichia coli* EC007; the plasmid was named as pEC-2; and through expanding propagation, the plasmid was extracted to obtain a plasmid pEC-2.

The plasmids pEC-2 and pXM-1 were simultaneously electro-transformed into *Corynebacterium glutamicum* GM4 competent cells, and experimental steps were the same as embodiment 1. Meanwhile, kana (primer kana-F/kana-R) and Cm (primer Cm-F/Cm-R) genes were verified; and a strain of which the two genes were verified accurate was named as *Corynebacterium glutamicum* MA2.

Figure 3:
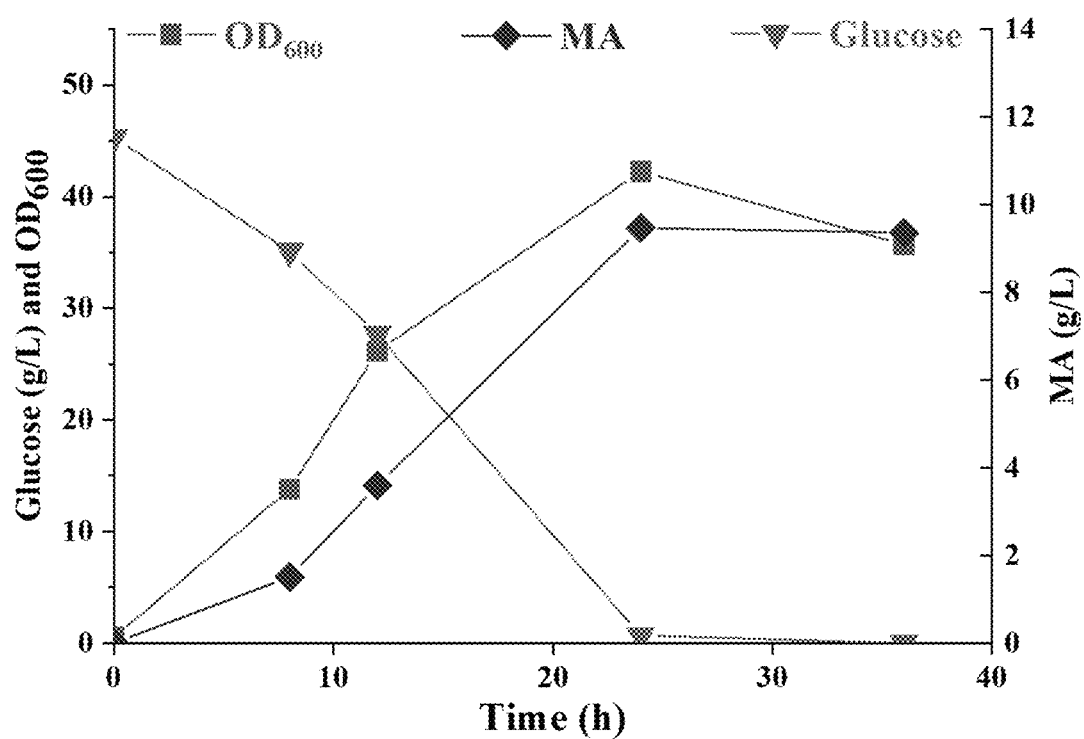
FIG. 3 shows growth and metabolism of a strain MA2 in fermentation of a 50 mL shaking flask and MA production situations in the present invention.

The *Corynebacterium glutamicum* MA2 was subjected to shaking flask fermentation verification in a 50 mL system, and a fermentation medium and fermentation operations were the same as embodiment 1. During shaking flask fermentation of the *Corynebacterium glutamicum* MA2 in the 50 mL system, MA of 9.4 g/L was produced by the strain (Table 3 and FIG. 3).

TABLE 3

| Time (h) | OD$_{600}$ | Glucose (g/L) | MA (g/L) |
|---|---|---|---|
| 0 | 0.50 | 45.30 | 0.00 |
| 8 | 13.80 | 35.10 | 1.51 |
| 12 | 26.15 | 27.65 | 3.60 |
| 24 | 42.25 | 0.70 | 9.47 |
| 36 | 35.70 | 0.00 | 9.37 |

Embodiment 3

A construction method of a genetic engineering bacterium for de novo synthesis of cis,cis-muconic acid by taking glucose as a substrate includes the following steps:

Genome DNA of *Pseudomonas putida* KT2440 was taken as a template; the segment catA was amplified by using a primer PP-catA-F/PP-catA-R (as shown in SEQ ID NO.76);

and *Pseudomonas putida* KT2440-derived catA with seamless cloning homologous arms in ligation with the plasmid was obtained.

Primer sequences were as follows:

PP-catA-F:
SEQ ID NO. 77
5'-CATATGAGCAAGATTCTCACCACCGC-3';;

PP-catA-R:
SEQ ID NO. 78
5'-CTTTTAGGCGAGATTGATGCCCAGG-3';.

A plasmid vector pEC-1 was linearized with a primer PEC-3-1F/PEC-3-1R to obtain a vector PECb, wherein primer sequences were as follows:

PEC-3-1F:
SEQ ID NO. 79
5'-CATCAATCTCGCCTAAAAGGAGGATATACATATGACCGCAC

C-3';;

PEC-3-1R:
SEQ ID NO. 80
5'-GGTGAGAATCTTGCTCATATGTATATCCTCCTTGAGCTCGA

ATTCTTCTGTTTCCTGTG-3';.

The gene amplification system and gene amplification procedures were the same as embodiment 1.

The vectors catA and PECb were ligated in the Gibson ligation manner in embodiment 1. An accurate plasmid was obtained through the above same verification step; and the accurate plasmid was named as pEC-3.

The plasmids pEC-3 and pXM-1 were simultaneously electro-transformed into *Corynebacterium glutamicum* GM4 competent cells, and experimental steps were the same as embodiment 1. kana (primer kana-F/kana-R) and Cm (primer Cm-F/Cm-R) genes were continuously verified; and a strain of which the two genes were verified accurate was named as *Corynebacterium glutamicum* MA3.

Figure 4:
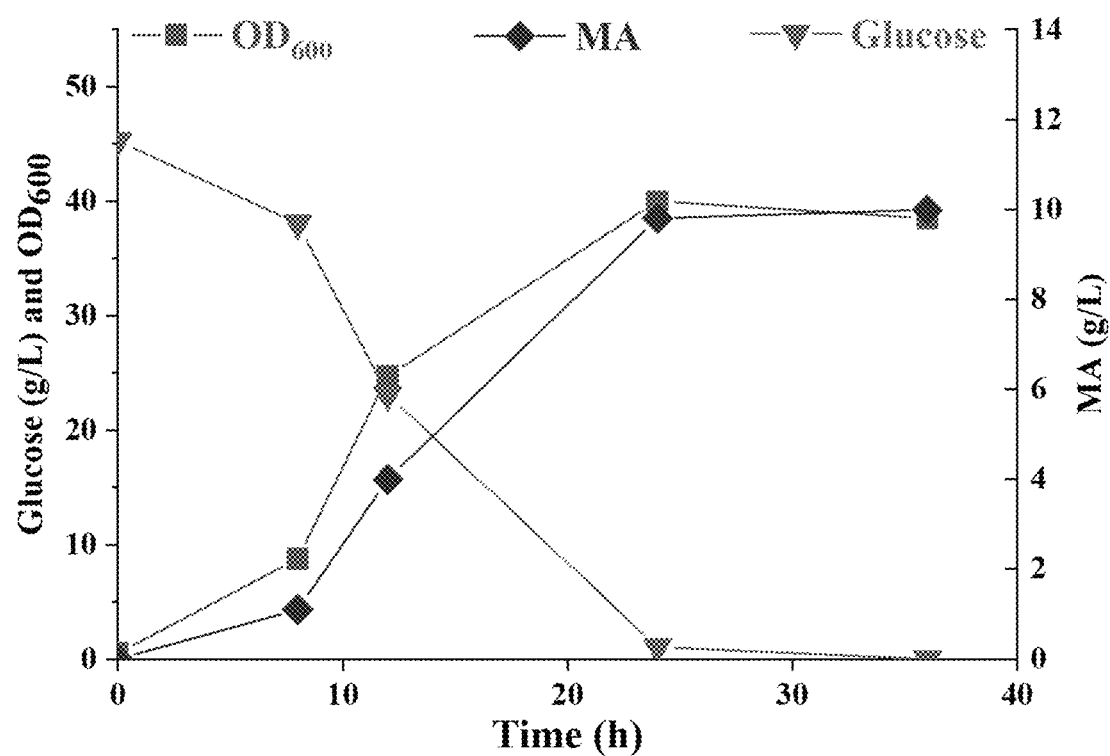
FIG. 4 shows growth and metabolism of a strain MA3 in fermentation of a 50 mL shaking flask and MA production situations in the present invention.

The *Corynebacterium glutamicum* MA3 was subjected to shaking flask fermentation verification in a 50 mL system, and a fermentation medium and fermentation operations were the same as embodiment 1. During shaking flask fermentation of the *Corynebacterium glutamicum* MA3 in the 50 mL system, MA of 10.0 g/L was produced by the strain (Table 4 and FIG. 4).

TABLE 4

| Time (h) | OD$_{600}$ | Glucose (g/L) | MA (g/L) |
|---|---|---|---|
| 0 | 0.50 | 45.25 | 0.00 |
| 8 | 8.77 | 38.07 | 1.10 |
| 12 | 24.71 | 23.09 | 4.00 |
| 24 | 40.00 | 1.07 | 9.80 |
| 36 | 38.50 | 0.00 | 9.99 |

Embodiment 4

A construction method of a genetic engineering bacterium for de novo synthesis of cis,cis-muconic acid by taking glucose as a substrate includes the following steps:

Genome DNA of *Escherichia coli* K-12 was taken as a template; the segment aroG was amplified by using a primer aroG-F/aroG-R (as shown in SEQ ID NO.81); and *Corynebacterium glutamicum*-derived aroG with seamless cloning homologous arms in ligation with the plasmid pXM-1 was obtained.

Primer sequences were as follows:

aroG-F:
SEQ ID NO. 82
5'-CATATGAATTATCAGAACGACGATTTACGCATCAAAG-3';;

aroG-R:
SEQ ID NO. 83
5'-CTTTTACCCGCGACGCGCTTT-3';.

A plasmid vector pXM-1 was linearized with a primer PXM-2-1F/PXM-2-1R to obtain a vector PXMa, wherein primer sequences were as follows:

PXM-2-1F:
SEQ ID NO. 84
5'-CGTCGCGGGTAAAAGGAGGATATACATATGTCCTCACGTAA

AG-3';;

PXM-2-1R:
SEQ ID NO. 85
5'-GTCGTTCTGATAATTCATATGTATATCCTCCTTCTACTTTTG

AGATTTGCCAGGATATCGACC-3';.

The gene amplification system and gene amplification procedures were the same as embodiment 1.

The vectors aroG and PXMa were ligated in the Gibson ligation manner in embodiment 1. An accurate plasmid was obtained through the above same verification step; and the accurate plasmid was named as pXM-2.

The plasmids pEC-1 and pXM-2 were simultaneously electro-transformed into *Corynebacterium glutamicum* GM4 competent cells, and experimental steps were the same as embodiment 1. kana (primer kana-F/kana-R) and Cm (primer Cm-F/Cm-R) genes were continuously verified; and a strain of which the two genes were verified accurate was named as *Corynebacterium glutamicum* MA4.

Figure 5:
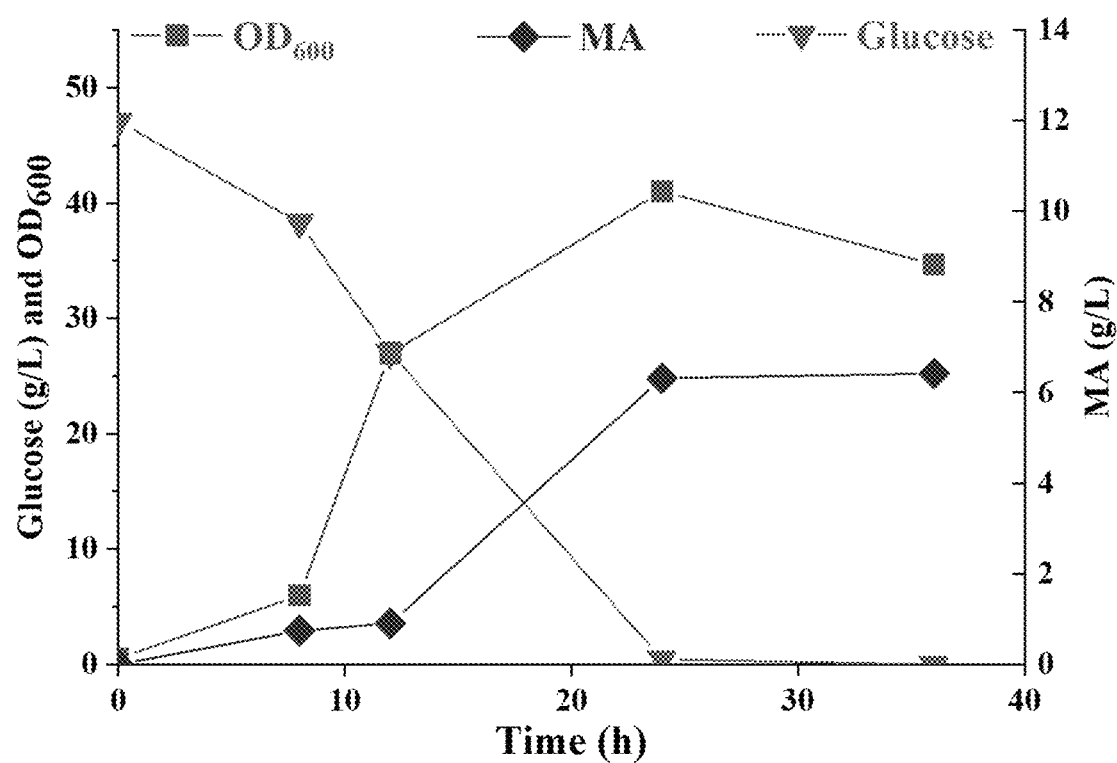
FIG. 5 shows growth and metabolism of a strain MA4 in fermentation of a 50 mL shaking flask and MA production situations in the present invention.

The *Corynebacterium glutamicum* MA4 was subjected to shaking flask fermentation verification in a 50 mL system, and a fermentation medium and fermentation operations were the same as embodiment 1. During shaking flask fermentation of the *Corynebacterium glutamicum* MA4 in the 50 mL system, MA of 6.4 g/L was produced by the strain (Table 5 and FIG. 5).

TABLE 5

| Time (h) | OD$_{600}$ | Glucose (g/L) | MA (g/L) |
|---|---|---|---|
| 0 | 0.50 | 47.06 | 0.00 |
| 8 | 6.00 | 38.29 | 0.74 |
| 12 | 27.00 | 27.01 | 0.90 |
| 24 | 41.00 | 0.44 | 6.32 |
| 36 | 34.67 | 0.00 | 6.42 |

Appearance time of an MA standard substance is 30.367 min; appearance time of a fermentation culture product of the genetic engineering strain prepared in embodiments 1-4 is 30.367 min and is consistent with the appearance time of an MA standard substance. Thus, it is proved that the fermentation product of the engineering strain is the target product, namely the MA.

The above description of the disclosed embodiments enables those skilled in the art to realize or use the present invention. Many modifications made to these embodiments will be apparent to those skilled in the art. General principles defined herein can be realized in other embodiments without departing from the spirit or scope of the present invention. Therefore, the present invention will not be limited to these embodiments shown herein, but will conform to the widest scope consistent with the principles and novel features disclosed herein.

What is claimed is:

1. A genetically engineered bacterium utilizing glucose for de novo synthesis of cis, cis-muconic acid, wherein the genetically engineered bacterium is *Corynebacterium glutamicum* ATCC13032 recombinantly modified to comprise a cis,cis-muconic acid pathway construction module and an intermediate high-yield module and further having knockouts of pyk, aroE, pcaG/H and CatB genes; wherein the cis,cis-muconic acid pathway construction module comprises a protocatechuate decarboxylase gene comprising SEQ ID NO: 37, an UbiX-like flavin prenyltransferase gene comprising SEQ ID NO: 68 or SEQ ID NO: 38, a 4-hydroxybenzoate decarboxylase subunit D gene comprising SEQ ID NO: 69 or SEQ ID NO: 39, and a catechol 1,2-dioxygenase gene comprising SEQ ID NO: 76 or SEQ ID NO: 35; and the intermediate high-yield module comprises a 3-dehydroquinate synthase gene comprising SEQ ID NO: 51, a 3-dehydroquinate dehydratase gene comprising SEQ ID NO: 52, and a transketolase gene comprising SEQ ID NO: 53.

2. The genetically engineered engineering bacterium according to claim 1, wherein the protocatechuate decarboxylase is the *Klebsiella pneumoniae*-derived protocatechuate decarboxylase;

the UbiX-like flavin prenyltransferase gene comprises SEQ ID NO: 38 is the *Klebsiella pneumoniae*-derived UbiX-like flavin prenyltransferase;

the 4-hydroxybenzoate decarboxylase subunit D gene comprises SEQ ID NO: 39 is the *Klebsiella pneumoniae*-derived 4-hydroxybenzoate decarboxylase subunit D; and the catechol 1,2-dioxygenase gene comprises SEQ ID NO: 35 is the *Corynebacterium glutamicum* endogenous catechol 1,2-dioxygenase;

the 3-dehydroquinate synthase is the *Corynebacterium glutamicum* endogenous 3-dehydroquinate synthase; and the 3-dehydroquinate dehydratase is the *Corynebacterium glutamicum* endogenous 3-dehydroquinate dehydratase.

3. The genetically engineered engineering bacterium according to claim 2, wherein the intermediate high-yield module further comprise a phospho-2-dehydro-3-deoxyheptonate aldolase gene having the nucleotide sequence as shown in SEQ ID NO: 81.

4. A construction method of a genetically engineered engineering bacterium according to claim 1, comprising the following steps:
   (1) taking *Corynebacterium glutamicum* ATCC13032 as a parental strain, and knocking out pyk, aroE, pcaG H and catB genes to obtain a modified *Corynebacterium glutamicum*; and
   (2) expressing the cis,cis-muconic acid pathway construction module and the intermediate high-yield module in the modified *Corynebacterium glutamicum*.

5. A method for producing cis,cis-muconic acid, the method comprising fermenting the genetically engineered engineering bacterium of claim 1 in a medium to produce cis,cis-muconic acid.

\* \* \* \* \*